(12) United States Patent
Kool

(10) Patent No.: US 9,416,155 B2
(45) Date of Patent: *Aug. 16, 2016

(54) DIRECT SENSING OF MOLECULAR SPECIES BY POLYFLUORS ON A DNA BACKBONE

(75) Inventor: Eric Todd Kool, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 244 days.

This patent is subject to a terminal disclaimer.

(21) Appl. No.: 13/515,481

(22) PCT Filed: Dec. 14, 2010

(86) PCT No.: PCT/US2010/060316
§ 371 (c)(1),
(2), (4) Date: Aug. 21, 2012

(87) PCT Pub. No.: WO2011/081939
PCT Pub. Date: Jul. 7, 2011

(65) Prior Publication Data
US 2012/0309107 A1    Dec. 6, 2012

Related U.S. Application Data

(60) Provisional application No. 61/284,210, filed on Dec. 14, 2009.

(51) Int. Cl.
*C07H 19/04*    (2006.01)
*C12Q 1/68*     (2006.01)
*C07H 21/00*    (2006.01)
*G01N 31/22*    (2006.01)
*G01N 33/58*    (2006.01)

(52) U.S. Cl.
CPC ............. *C07H 21/00* (2013.01); *G01N 31/22* (2013.01); *G01N 33/582* (2013.01)

(58) Field of Classification Search
CPC ........................................... C07H 21/00
USPC ........................................ 536/26.6; 435/6.1
See application file for complete search history.

(56) References Cited

U.S. PATENT DOCUMENTS 6,479,650 B1    11/2002    Kool
6,485,703 B1    11/2002    Cote et al.
(Continued)

OTHER PUBLICATIONS

Freund; et al. "A chemically diverse conducting polymer-based 'electronic nose'", PNAS (Mar. 1995), 92 (6):2652-2656.
(Continued)

*Primary Examiner* — Jezia Riley
(74) *Attorney, Agent, or Firm* — Glenn J. Foulds; Bozicevic, Field & Francis LLP

(57) ABSTRACT

Nucleoside analogs are provided; and fluorescent sensors comprising the nucleoside analogs. The sensors comprise multiple chromophores built on a DNA backbone, in which all the natural DNA bases are replaced by excimeric or exciplex-forming fluorophores, ligands, quenchers and spacers in thousands of combinations. The sensors find use in the detection and identification of target analytes by fluorescence, e.g., detection of metal ions, neutral organic compounds and anions. The sensors find use in the detection and identification of molecular species in the vapor or gaseous phase, or the liquid phase. The sensors find use in qualitative and quantitative screening and detection methods.

16 Claims, 17 Drawing Sheets

(56) References Cited

U.S. PATENT DOCUMENTS

| | | | |
|---|---|---|---|
| 6,670,193 B2 | 12/2003 | Kool | |
| 8,268,977 B2* | 9/2012 | Kool | C07H 7/04 435/6.1 |
| 2002/0160411 A1 | 10/2002 | Kool | |
| 2003/0068275 A1 | 4/2003 | Lippard et al. | |
| 2005/0064529 A1 | 3/2005 | Kwon | |
| 2005/0106594 A1 | 5/2005 | Ellington et al. | |
| 2007/0049761 A1 | 3/2007 | Wilson et al. | |
| 2009/0023148 A1 | 1/2009 | Moyle et al. | |

OTHER PUBLICATIONS

Janzen; et al. "Colorimetric sensor arrays for volatile organic compounds", Anal Chem (Jun. 2006), 78 (11):3591-3600.

Kim; et al. "Sensing metal ions with DNA building blocks: fluorescent pyridobenzimidazole nucleosides", JACS (May 2006), 128(18):6164-6171.

White; et al. "Solid-state, dye-labeled DNA detects volatile compounds in the vapor phase", PLoS Biol (Jan. 2008), 6 (1):e9.

* cited by examiner (buffer alone)

(buffer + 10 uM Cu2+)

(difference image: overlay inverse)

| Entry | Analyte | Beads | Before | After | diff | Sequences: 5' → 3' |
|---|---|---|---|---|---|---|
| 1 | Acrolein | FS-1 | | | | DHT-I-E-DHT |
| | | FS-2 | | | | Y-E-DHT-DHT |
| 2 | Methyl iodide | FS-4 | | | | E-DHT-S-E |
| | | FS-5 | | | | Y-S-Y-K |
| 3 | Acrylonitrile | FS-9 | | | | S-Y-Y-E |
| 4 | Ethyl isocyanate | FS-15 | | | | Y-DHT-Y-DHT |
| 5 | Mesitylene | FS-17 | | | | Y-Y-S-B |
| | | FS-18 | | | | Y-E-B-Y |
| 6 | Propionic acid | FS-19 | | | | Y-DHT-B-S |
| | | FS-21 | | | | S-DHT-E-S |
| 7 | Nitrobenzene | FS-24 | | | | Y-S-E-S |
| | | FS-25 | | | | Y-Y-E-K |
| 8 | dimethylaniline | FS-26 | | | | Y-E-B-I |
| | | FS-27 | | | | S-E-B-DHT |

FIG. 7

DIRECT SENSING OF MOLECULAR SPECIES BY POLYFLUORS ON A DNA BACKBONE

GOVERNMENT RIGHTS

This invention was made with Government support under grant GM067201 awarded by the National Institutes of Health. The Government has certain rights in this invention.

BACKGROUND OF THE INVENTION

Fluorescence methods are widespread in chemistry and biology. The methods give useful information on structure, distance, orientation, complexation, and location for biomolecules. Fluorescence based sensors provide sensitive means of determining the presence of compounds of interest in a sample. Various signal transduction methodologies can be use in measuring the response, where the sensor can produce a detectable change in fluorescence upon interacting with an analyte. Fluorescent sensors can provide desirable properties such as water solubility, low detection limits, and high selectivity for a desired analyte, where the analyte can be a small molecule, an enzyme, a catalytic metal, and the like.

It is clear that there is more than one type of interaction between light-absorbing molecules. One useful class of interaction is Forster energy transfer, also called fluorescence resonance energy transfer, or FRET. In this interaction, fluorescence excitation energy is transferred from a donor to an acceptor fluorophore. The extent of transfer depends on distance and on overlap in emission and absorption of donor and acceptor. FRET can occur over relatively long distances (tens of Angstroms). A second form of energy transfer is exciplex formation, which involves bonding between an excited-state fluorophore and a neighboring ground-state fluorophore, yielding a delocalized excited state. This results in a long red shift to fluorescence. Exciplexes can form only between molecules in direct contact or very nearly so. Exciplexes between two of the same molecules are known as excimers. Another class of interaction involving a fluorophore is quenching, in which a molecule causes the quantum yield of nearby fluorescent molecule to be lowered.

Chemists have in the past 10-20 years developed molecular sensors for specific chemical species. Fluorescent sensors have been developed that function in identifying and quantitating individual metal cations (such as $Cd^{2+}$ or $Hg^{2+}$)[2,3] at low micromolar, and sometimes nanomolar, concentrations. Fewer examples exist for fluorescence sensing of toxic anions, although there are a few recent reports of sensors for cyanide and peroxynitrite.[4,5] Chemists and engineers have also worked recently on "artificial nose"/"artificial tongue" designs, where organic vapors are adsorbed by polymers or groups of compounds, and result in fluorescence quenching, or in color changes in nonfluorescent materials. Such approaches have worked for specific species, such as polynitrotoluenes from explosives, and have been used for distinguishing organics in soft drinks. For example, sensors find use in remediation of industrial work and storage sites. At such sites frequent monitoring is required in addressing spills, leakage and contamination, and restoring the sites to a clean condition, to minimize environmental and human exposure.

Despite this previous work, there is no general fluorescent sensor design that can sense a wide variety of species such as cations, anions, vapors, gases, and neutral organics. Moreover, making sensor molecules is usually a laborious process involving multiple steps of organic synthesis by hand. In addition, the use of different traditional sensors would require different excitation wavelengths and filters. The present invention addresses all of these needs, by providing oligomeric sensor molecules that are easily constructed on an automated synthesizer. The large diversity of these molecules allows for specific sequences that yield a signal for a wide variety of molecular species; moreover, many of the molecules can be excited by one wavelength of light.

The present invention provides nucleoside analogs and sensors incorporating the subject nucleoside analogs. Combinatorial sequences of fluorophores built on a nucleic acid backbone may be generated and screened to identify sensors of molecular species with suitable fluorescent properties. The present invention provides sensors for simultaneous multiplexed detection of several molecular species.

Related Publications

Kool, U.S. Pat. Nos. 6,670,193 and 6,479,650, disclose fluorescent nucleoside analogs and combinatorial fluorophore arrays comprising same.

Kool et al., J. Am. Chem. Soc. 2006, 128, 6164-6171 disclose the sensing of metal ions with DNA building blocks such as fluorescent pyridobenzimidazole nucleosides.

Ellington, US Application 20050106594, disclose methods of selecting aptamer beacons in vitro using single-stranded nucleic acid species comprising a fluorphore and a random region of N nucleotides.

White et al., 2008 "Solid-State, Dye-Labeled DNA Detects Volatile Compounds in the Vapor Phase," PLoS Biol 6(1): e9. doi:10.1371/journal.pbio.0060009 disclose the detection of odors by changes in fluorescence of dye-labeled, solid-state DNA dried onto a surface. Suslick et al., Anal Chem. 2006, 78(11):3591-600 disclose a colorimetric sensor array of chemoresponsive dyes for the detection and identification of volatile organic compounds (VOCs). Freud and Lewis, PNAS 92, pp. 2652-2656, 1995 disclose a chemically diverse conducting polymer-based 'electronic nose' sensitive to the identity and concentration of various vapors in air.

SUMMARY OF THE INVENTION

Nucleoside analogs are provided; and sensors comprising the nucleoside analogs. Sensors of the invention generally comprise multiple chromophores built on a DNA backbone, in which all the natural DNA bases are replaced by fluorophores, ligands, quenchers and spacers. Sensors of the invention are generally small and built on a DNA synthesizer in thousands of combinations of nucleoside analogs, in discrete lengths, e.g., lengths of from 2 to 20 residues, usually lengths of from 2 to 8, such as 2, 3, 4, 5, 6, 7, or 8 residues. Sensors of the invention find use in the detection and identification of target analytes by fluorescence, e.g., in the detection of metal ions, neutral organic compounds and anions. Sensors of the invention find use in the detection and identification of molecular species in the vapor or gaseous phase, or the liquid phase.

Sensors of the invention are small water-soluble oligomers (called oligofluors, oligodeoxyfluorosides, or ODFs) comprising fluorophores, ligands, quenchers and spacers arranged on a backbone; which exhibit a change in fluorescence upon binding of a target analyte, e.g., a change in the fluorescence emission intensity or emission wavelength. In some embodiments sensors of the invention include at least one metal ion bound to the oligomer. The sensors find use in qualitative and quantitative screening and detection methods.

In some embodiments, the sensor of the invention is of the structure of Formula I:

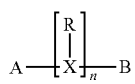 (I)

where A and B are each independently a backbone group, linker, substrate, or binding moiety, and may be absent or present;

X is a backbone group;

n is 2 to 20; and

R is a chromophore, a fluorophore, a ligand, a quencher or a spacer, where each R can be the same or different. In some embodiments of Formula I, R is independently selected from one or more of the following structures:

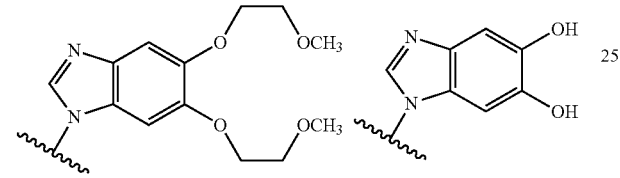

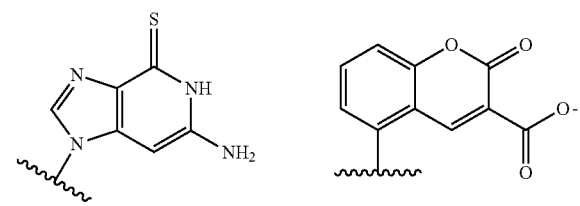

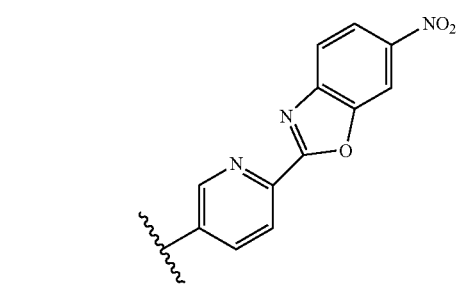

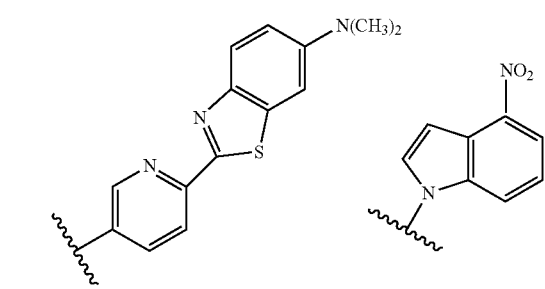

-continued

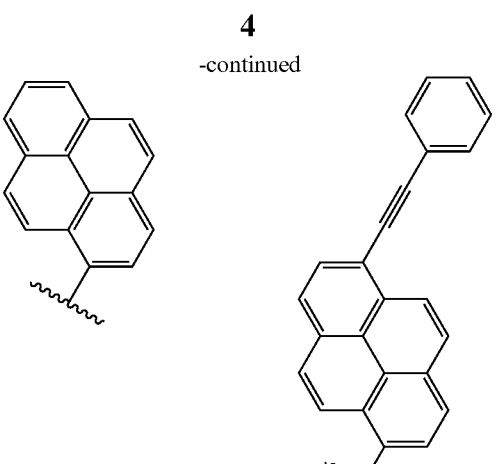

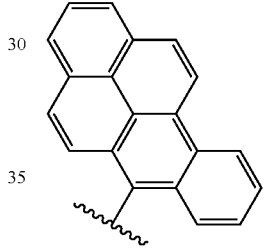

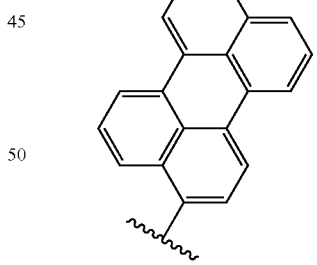

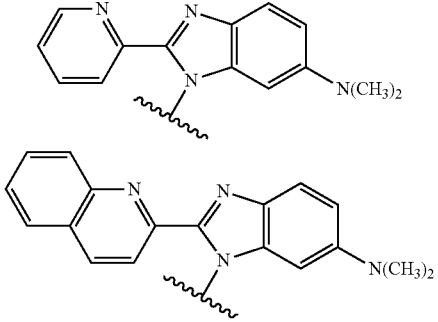

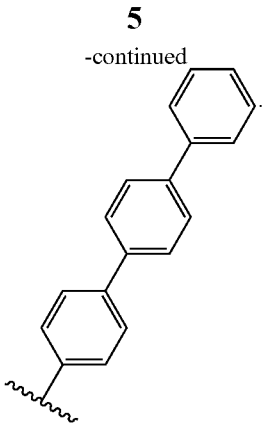

BRIEF DESCRIPTION OF THE DRAWINGS

FIG. 7 illustrates sensors identified for various vapors, and their responses. Images of the beads before and after exposure to the vapor are shown along with the digitally generated difference image.

DETAILED DESCRIPTION OF THE EMBODIMENTS

Figure 1:
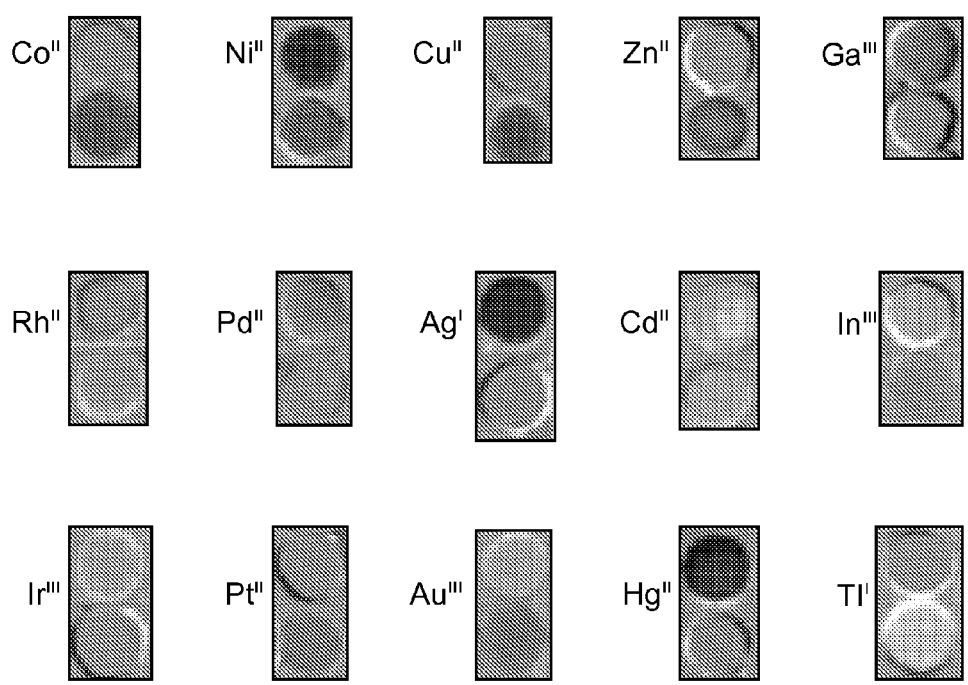
FIG. 1 illustrates the response of oligodeoxyfluoroside sensors to 10 μM of various metal cations.
Figure 2:
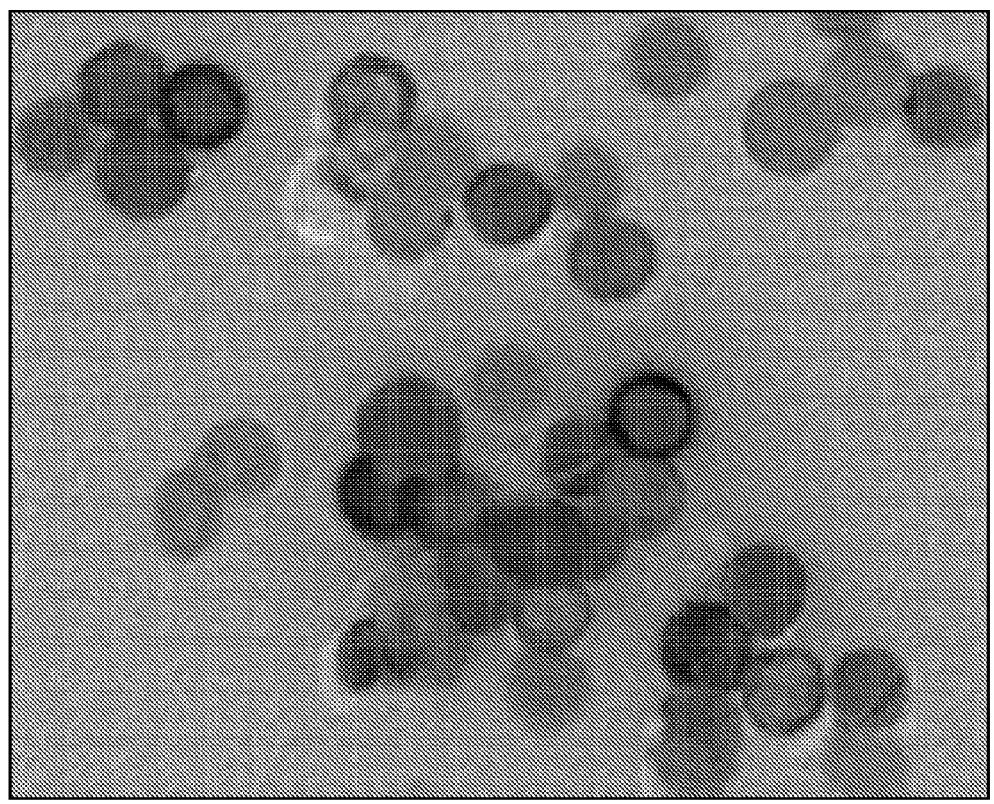
FIG. 2 illustrates the difference image of an oligodeoxyfluoroside library after exposure to fluoronitrobenzene. The response is indicated by color/intensity; for example, a red color indicates a redshift upon analyte binding, while blue indicates a blueshift.
Figure 3:
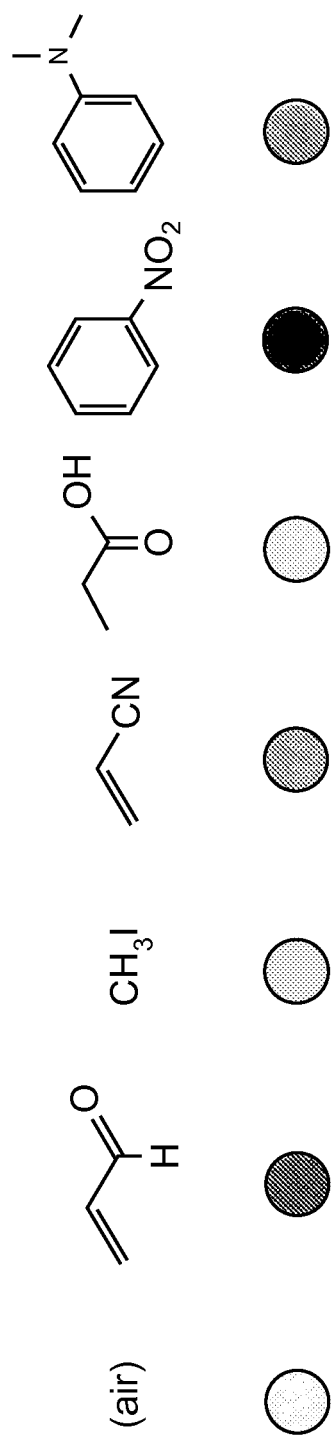
FIG. 3 illustrates examples of organic compounds tested for vapor sensing, along with the response of one sensor selected for that analyte. The bead images indicate sensor response (initial emission digitally substracted from emission after exposure to analyte).

Nucleoside analogs are provided; and sensors comprising the nucleoside analogs. Sensors of the invention generally comprise multiple chromophores built on a DNA backbone, in which all the natural DNA bases are replaced by fluorophores, ligands, quenchers and spacers. Sensors of the invention are generally small and built on a DNA synthesizer in thousands of combinations of nucleoside analogs, in discrete lengths.

The use of DNA labeled with fluorophores has been reported as a sensor for gases (White et al., supra.) The DNAs in that study were 20-24 nucleotides long, incorporated many natural DNA bases, and utilized only one type of fluorescent label at a time, which label was not attached to the DNA. In the study there was only one type of fluorescence response to the gases (changes in intensity, not wavelength). As a result, the fluorescence responses of those sensors makes it difficult to differentiate between different gases or vapors, since the same type of response occurs with many analytes. Since only one type of response is seen, it is not at all obvious how one would modify that type of sensor to give different types of distinct responses to different gases or vapors. In addition, the authors propose that the natural DNA structure is involved in the recognition and binding. Is it thus not obvious that removing all the DNA bases (as in the current invention) would still allow for any type of useful sensing—indeed, it was reported that response was abrogated by leaving out DNA. Moreover, the authors did not demonstrate any sensing of metal ions or of anions, and they did not demonstrate any sensing in the solution phase.

This is very different from the ODF sensors of the current invention, where a wide array of fluorescence responses are seen: quenching, lighting up, and color shifts to shorter or longer wavelengths. This diversity of response allows one to differentiate between different analytes; for example, it is shown that even one sensor molecule can yield distinct responses for different analyte vapors. The compounds of the present invention contain multiple types of fluorophores, which are chemically attached to one another in a DNA-like oligomer structure. The fluorophores can directly stack on one another by virtue of the position of attachment on the deoxyribosephosphate backbone. The compounds of the invention are structurally distinct because they can function in the absence of natural DNA nucleoside components. Finally, the compounds of the invention are much smaller than the previous DNA sensors, allowing them to be made more easily and cheaply. Surprisingly, the ODF sensors of the invention are able to recognize and respond to analytes even in the absence of DNA bases for recognition. Finally, the sensors of the invention can function in aqueous solution.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, compounds which are "commercially available" may be obtained from standard commercial sources including Acros Organics (Geel Belgium), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Invitrogen (Carlsbad, Calif.), Applied Biosystems, Inc. (Foster City, Calif.), Glen Research (Sterling, Va.), Biosearch Technologies (Novato, Calif.), Anaspec (Fremont, Calif.) and Berry & Associates (Dexter, Mich.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, phenyl, aryl, alkenyl, alkynyl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$. Typical substituents include, but are not limited to, —X, —R$^8$ (with the proviso that R$^8$ is not hydrogen), —O—, =O, —OR$^8$, —SR$^8$, —S$^-$, =S, —NR$^8$R$^9$, =NR$^8$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^8$, —OS(O$_2$)O$^-$, —OS(O)$_2$R$^8$, —P(O)(O—)$_2$, —P(O)(OR$^8$)(O$^-$), —OP(O)(OR$^8$)(OR$^9$), —C(O)R$^8$, —C(S)R$^8$, —C(O)OR$^8$, —C(O)NR$^8$R$^9$, —C(O)O$^-$, —C(S)OR$^8$, —NR$^{10}$C(O)NR$^8$R$^9$, —NR$^{10}$C(S)NR$^8$R$^9$, —NR$^{11}$C(NR$^{10}$)NR$^8$R$^9$ and —C(NR$^{10}$)NR$^8$R$^9$, where each X is independently a halogen.

The compounds of the invention may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

"Quencher" refers to any fluorescence-modifying group that can alter at least partly the light emitted by a fluorescent group. A sensor having a quencher may also comprise one or more donor fluorophores. The quencher may alter the light emission by the fluorescent group by any known mechanism including without limitation resonance energy transfer (e.g. Förster resonance energy transfer), reductive electron transfer, oxidative electron transfer, excited state reactions, complex formation, collision quenching, electron exchange (e.g. Dexter energy exchange), etc. The quencher may or may not be a fluorescent molecule, it being sufficient that the quencher prevents radiative dexcitation of the excited fluorophore. A fluorophore-quencher pair may be chosen such that the quencher can donate or accept charge to or from the excited-state fluorophore. Any fluorescence quencher can be used, for example the quencher can be a diazo-dye e.g. DABSYL (dimethylamino-azobenzene-sulfonyl) group, DABCYL (dimethylamino-azobenzene-carboxy), BLACK HOLE QUENCHERS™, DANSYL (5-dimethylaminonaphthalene-sulfonyl); DIMAPDABSYL ((p-dimethylamino-phenylazo) azobenzenesulfonyl), any of which may comprise substituents such as amino, dialkylamino, nitro, fluoro, and cyano groups; anthraquinone, nitrothiazole, viologen, and nitroimidazole compounds; rhodamine dyes (e.g., tetramethyl-6-carboxyrhodamine (TAMRA)); ROX; cyanine; coumarin; BODIPY dyes; fluorescein dyes; ALEXA™ dyes; QXL™ dyes; and the like.

"Fluorophore" refers to a molecule that, when excited with light having a selected wavelength, emits light of a different wavelength, which may emit light immediately or with a delay after excitation. Example of fluorophores, include, without limitation, fluorescein dyes, e.g., 5-carboxyfluorescein (5-FAM), 6-carboxyfluorescein (6-FAM), 2',4',1,4-tetrachlorofluorescein (TET), 2',4',5',7',1,4-hexachlorofluorescein (HEX), and 2',7'-dimethoxy-4',5'-dichloro-6-carboxyfluorescein (JOE); cyanine dyes, e.g. Cy3, CY5, Cy5.5, QUASAR™ dyes etc.; dansyl derivatives; rhodamine dyes e.g. 6-carboxytetramethylrhodamine (TAMRA), CAL FLUOR™ dyes, tetrapropano-6-carboxyrhodamine (ROX). BODIPY fluorophores, ALEXA™ dyes, Oregon Green, pyrene, perylene, benzopyrene, squarine dyes, coumarin dyes, luminescent transition metal and lanthanide complexes and the like. The term fluorophores includes excimers and exciplexes of such dyes.

As used herein, "nucleoside" also encompasses "nucleotide" which is a phosphate ester of a nucleoside. Thus, any reference herein to "nucleoside" or "nucleoside analog" is also meant to include "nucleotide" or "nucleotide analog". As used herein "nucleoside" is also meant to include nucleotide triphosphates.

"Oligonucleotide", or "polynucleotide" means either DNA, RNA, single-stranded or double-stranded, and derivatives thereof, including, but are not limited to: 2'-position sugar modifications e.g. 2'-OMe RNA, 2'-F RNA; phosphate modifications e.g. phosphorothioates, phosphorodithioates, phosphonates; propynyl additions, for example at the at the 5 position of pyrimidines; 5-position pyrimidine modifications, 7- or 8-position purine modifications, modifications at exocyclic amines, 5-methyl cytosine; 5 bromo-cytosine; alkynyl uridine and cytosine; substitution of 4-thiouridine, substitution of 5-bromo or 5-iodo-uracil; backbone modifications, including peptide nucleic acids (PNA), locked nucleic acids (LNA), etc., methylations, morpholino derivatives; phosphoroamidate derivatives; stabilizing bases e.g. G-clamp, 2,6-diaminopurine; fluorophore modifications; unusual base-pairing combinations such as the isobases isocytidine and isoguanidine and the like. Derivatives can also include 3' and 5' modifications such as capping, addition of a tether with a functional group, biotinylation, cholesterol, addition of a fluorophore. Individual nucleotide residues within the polynucleotide sequence may be modified, for example, modified at the nucleobase, or on the backbone, to include a group such as a fluorophore or a biotin, etc.

"Backbone group" refers to groups that make up the backbone of an oligonucleotide or oligonucleotide analog as described herein, and those backbone groups which are known in the art. For example, a deoxyribosephosphate group is a backbone group that can be arranged in a sequence to form a DNA backbone with phosphodiester linkages.

Sensors may be covalently or non-covalently linked to a variety of known reactive groups, e.g. thiols, amines, NHS esters, isothiocyanates, maleimides, alkynes, azides, etc.; supports; substrates; and binding moieties. One of skill in the art will understand that a molecule such as a protein, or polynucleotide, may serve as one or both of binding moiety and support.

In some embodiments, a sensor is attached to a solid support (for example: beads, membrane, 96-well plate, array substrate, filter paper and the like) directly or indirectly. Suitable solid supports may have a variety of forms and compositions and derive from naturally occurring materials, naturally occurring materials that have been synthetically modified, or synthetic materials. Examples of suitable support materials include, but are not limited to, CPG, silicas, teflons, glasses, polysaccharides such as cellulose, nitrocellulose, agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate; matrix proteins such as collagens, keratins, etc., and the like.

Binding moieties may include, without limitation, specific and non-specific binding. The term "specific binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

Examples of binding moieties include, but are not limited to antibodies, lymphokines, cytokines, receptor proteins such as CD4 and CD8, solubilized receptor proteins such as soluble CD4, hormones, growth factors, peptidomimetics, synthetic ligands, and the like which specifically bind desired targets, and nucleic acids which bind corresponding nucleic acids through base pair complementarity. Targeting moieties of particular interest include peptidomimetics, peptides, antibodies and antibody fragments (e.g. the Fab' fragment); DNA, RNA and analogs thereof.

The linkers of the invention are useful in providing a cleavable or non-cleavable attachment of a sensor to a substrate. By "solid substrate" or "solid support" is meant any surface to which the probes of the invention are attached. A variety of solid supports or substrates are suitable for the purposes of the invention, including both flexible and rigid substrates. By flexible is meant that the support is capable of being bent, folded or similarly manipulated without breakage. Examples of flexible solid supports include nylon, nitrocellulose, polypropylene, polyester films, such as polyethylene terephthalate, etc. Rigid supports do not readily bend, and include glass, fused silica, quartz, acrylamide; plastics, e.g. polytetrafluoroethylene, polypropylene, polystyrene, polystyrene and sulfonated polystyrene-divinyl benzene, quaternized product of chloromethylated polystyrene-divinyl benzene, PEG-polystyrene, PEG, polycarbonate, and blends thereof, and the like; metals, e.g. gold, platinum, silver, and the like; etc. The substrates can take a variety of configurations, including planar surfaces, filters, fibers, membranes, beads, particles, dipsticks, sheets, rods, etc.

"Oligofluor" refers to an oligomer comprising multiple fluorophores, ligands, quenchers and spacers arranged on a backbone. "Oligofluoroside" refers to an oligofluor comprising a sequence of fluorescent nucleoside analogs. "Oligodeoxyfluoroside" (ODF) refers to an oligofluoroside comprising 2-deoxyribose sugar moieties as backbone groups, for example, as in a DNA backbone. The oligofluors may include in the sequence one or more non-fluorescent residues, such as, a spacer, a ligand, a non-fluorescent quencher, or a natural DNA or RNA nucleoside. As used herein, the term "fluorescent nucleoside" is used to refer to a "nucleoside analog" comprising a fluorescent group, e.g., a fluorescent cyclic compound attached to the C1 position of the sugar moiety.

"Ligand" refers to a group that can bind to, or has affinity for, an analyte of interest. For example, a ligand is a group that will bind a metal ion of interest by coordination. For example, a ligand is a group that is capable of forming a hydrogen-bond or a hydrophobic interaction with an organic molecule of interest. For example, a ligand is a group that is capable of forming an electrostatic interaction with an anion of interest.

Compositions

In some embodiments, a sensor has the structure of Formula I:

where A and B are each independently a reactive group, backbone group, linker, substrate, or binding moiety, and may be absent or present;

X is a backbone group;

n is 2 to 20; and

R is a chromophore, a fluorophore, a ligand, a quencher or a spacer. In some embodiments of Formula I, R is independently selected from one or more of the following structures:

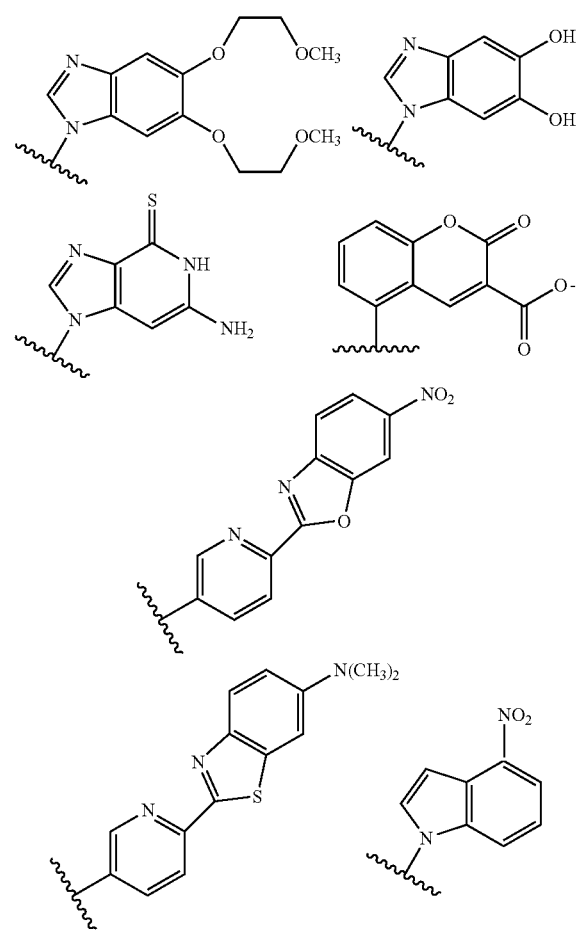

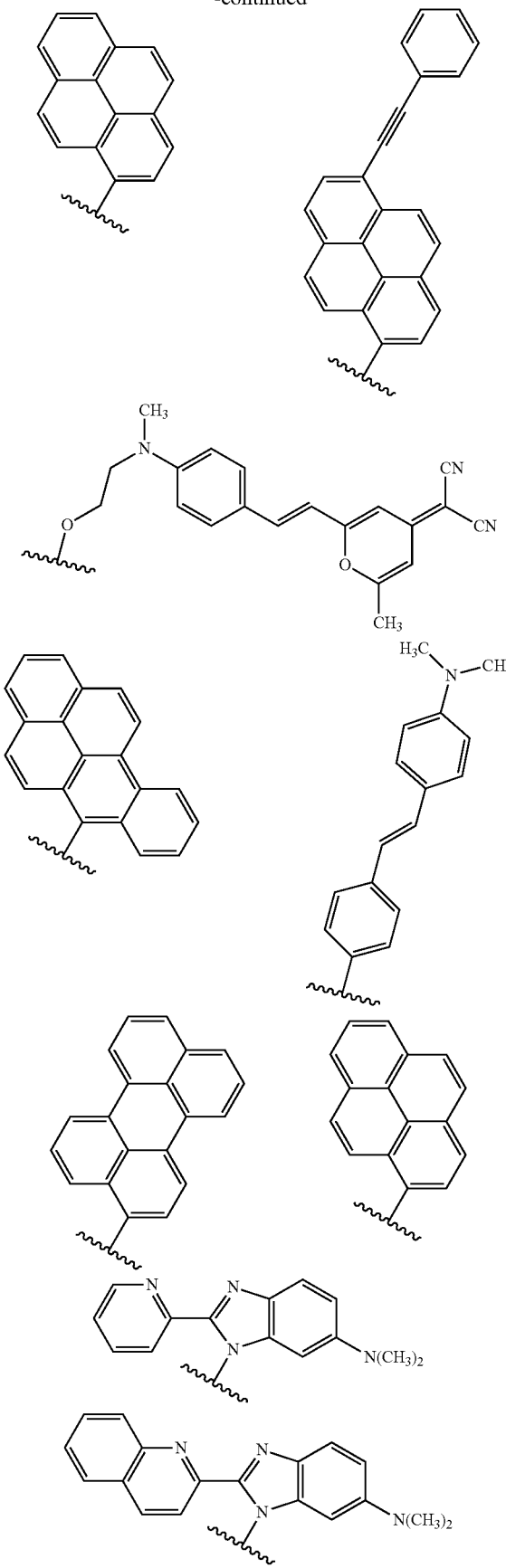

In certain embodiments, a sensor is of the structure of Formula I, where X is a sugar-phosphate, a phosphodiester, a phosphorothioate, a phosphotriester, a locked nucleic acid (LNA) backbone group; a morpholino; a 2'-O-methyl RNA backbone group, or a peptide nucleic acid backbone group. In certain embodiments, X is ribosephosphate or deoxyribose-phosphate such that the backbone groups Xn comprise a DNA or RNA backbone, and where R is connected to X via the C1 position of the ribose or deoxyribose.

In some embodiments, a sensor of the structure of Formula I includes at least one bound metal ion.

In some embodiments, the fluorescence emission intensity or emission wavelength of a sensor of the structure of Formula I changes following binding of a target analyte.

In certain embodiments, a sensor is of the structure of Formula I, where the target analyte is in vapor phase, gas phase or solution phase. In certain embodiments, the target analyte is a metal ion, an anion or an organic molecule.

In certain embodiments, a sensor is of the structure of Formula I, where the target analyte is a metal ion, and where the metal ion is $Zr^{4+}$, $Hf^{4+}$, $V^{3+}$, $Mo^{3+}$, $W^{4+}$, $Mn^{2+}$, $Ru^{3+}$, $OS^{3+}$, $CO^{3+}$, $Ni^{2+}$, $Pd^{2+}$, $Pt^{2+}$, $Cu^{2+}$, $Ag^+$, $Zn^{2+}$, $Cd^{2+}$, $Hg^{2+}$, $Be^{2+}$, $Ba^{2+}$, $Al^{3+}$, $In^{3+}$, $Tl^+$, $Ge^{4+}$, $Sn^{4+}$, $Pb^{2+}$, $As^{3+}$, $Sb^{5+}$, $Se^{4+}$, $Fe^{2+}$, $Fe^{3+}$, $Au^+$, $Au^{3+}$, $Te^{2+}$ or $UO_2^{2+}$, $Na^+$, $K^+$, $Rb^+$, $Cs^+$, $Mg^{2+}$, $Ca^{2+}$, $Sr^{2+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Ho^{3+}$, $Dy^{3+}$, $Er^{3+}$, $Tm^{3+}$, $Yb^{3+}$, $Lu^{3+}$.

In certain embodiments, a sensor is of the structure of Formula I, where the target analyte is an anion, where the anion is $CN^-$, $ClO_4^{2-}$, $HPO_4^{2-}$, $AsO_3^{3-}$, $OCl-$, $NO_2^-$, $NO_3^-$, $Br_3^-$, $SCN^-$, $F^-$, $N_3^-$, $SeO_3^{2-}$, $CrO_4^{2-}$, $MnO_4^-$, $BO_3^{3-}$, $CH_3CO_2^-$, or oxalate.

In certain embodiments, the organic molecule is a petroleum component, a petroleum additive, a sulfur compound found in oil, a cleaner/degreaser, a solvent, a polychlorinated hydrocarbon, a pesticide or an herbicide.

In certain embodiments, the organic molecule is unidentified component of a mixture which gives the mixture a distinguishing characteristic; for example, molecules that are characteristic of spoiled milk or fermented juice as compared with unspoiled or non-fermented products.

In some embodiments, a sensor is of the structure of Formula I, where the sensor is linked to a substrate through A or B.

In some embodiments, a method for detection of an analyte of interest includes: contacting a sample suspected of comprising the analyte of interest with the sensor according to claim 1, for a time and under conditions sufficient to permit binding of the analyte of interest to the sensor; and detecting a change in fluorescence emission intensity or emission wavelength of the sensor.

In some embodiments, libraries of ODF sensors are built using combinatorial methods; they are produced on PEG-polystyrene beads. In some embodiments, libraries of the invention are built on beads so that each bead has only one type of compound on it. In some embodiments, a sensor of the invention is a tetramer, where 5-12 different monomer species can occupy any position. For example, with 5 different monomers, a tetramer sensor can be built in 54 combinations (libraries 625 different compounds). For example, with 11 monomers, a tetramer sensor library can contain >14,000 different compounds.

In some embodiments, a library of sensors of the invention is screened by examining the beads under a microscope. An image is taken both before and after exposure to the analyte of interest; a difference map shows which beads respond (with a color shift, or change in intensity). The best-responding beads are picked out and decoded to identify the specific sensor sequence. In this way effective sensors of many different analytes can be identified quickly and easily.

In some embodiments, a sensor detects metals. ODF metal sensors can contain fluorescent monomers as well as aromatic metal ligands. In some cases, metals bind to the ligands and interact electronically with the neighboring fluorophores, resulting in a fluorescence change. Metal sensing can be done in aqueous solution.

In some embodiments, a sensor detects neutral organic compounds in the vapor phase. In some cases, ODF vapor sensors contain fluorophores as well as spacers, hydrogen bonding monomers and quenchers. In certain embodiments, sensors of different organic compounds respond with strong color shifts and/or changes in fluorescence intensity. In some cases, a small set of ODFs can be used to generate patterns of responses, constituting a type of "artificial nose".

In some embodiments, a sensor detects anions, e.g., toxic anions, such as cyanide, azide, perchlorate, nitrate, etc. In some cases, sensors of anions incorporate strongly bound metals in the ODF. Anions will bind the metals, changing their electronic environment and thus changing the electronic character of the ODF as a whole.

In some embodiments, a sensor detects gases, e.g., toxic gases such as ammonia, HCN, hydrogen sulfide, carbon monoxide, phosphine, nitric oxide, ozone, etc. In some cases, gas sensors of ODFs incorporate strongly bound metals as well as fluorophores in the ODF. Gases bind the metals, resulting in changes to the electronic properties of the metal, its ligand, and the fluorophores nearby.

The present invention provides fluorescent labels for nucleic acids which, rather than modifying an existing nucleic acid base, replace one or more DNA or RNA bases with a fluorescent cyclic compound. In accordance with the present invention, there are provided fluorescent nucleoside and nucleotide analogs comprising a fluorescent cyclic compound or ligand attached to a carbon of a sugar moiety. The sugar moiety may include, for example, pentose or hexose, such as ribose or deoxyribose. In some embodiments, the fluorescent cyclic compound is attached to the C1 position of the sugar moiety. The fluorescent cyclic compound or ligand attached to the sugar moiety may include such molecules as the following, where the fluorescent cyclic compound or ligand is attached to the sugar via any available position of the ring:

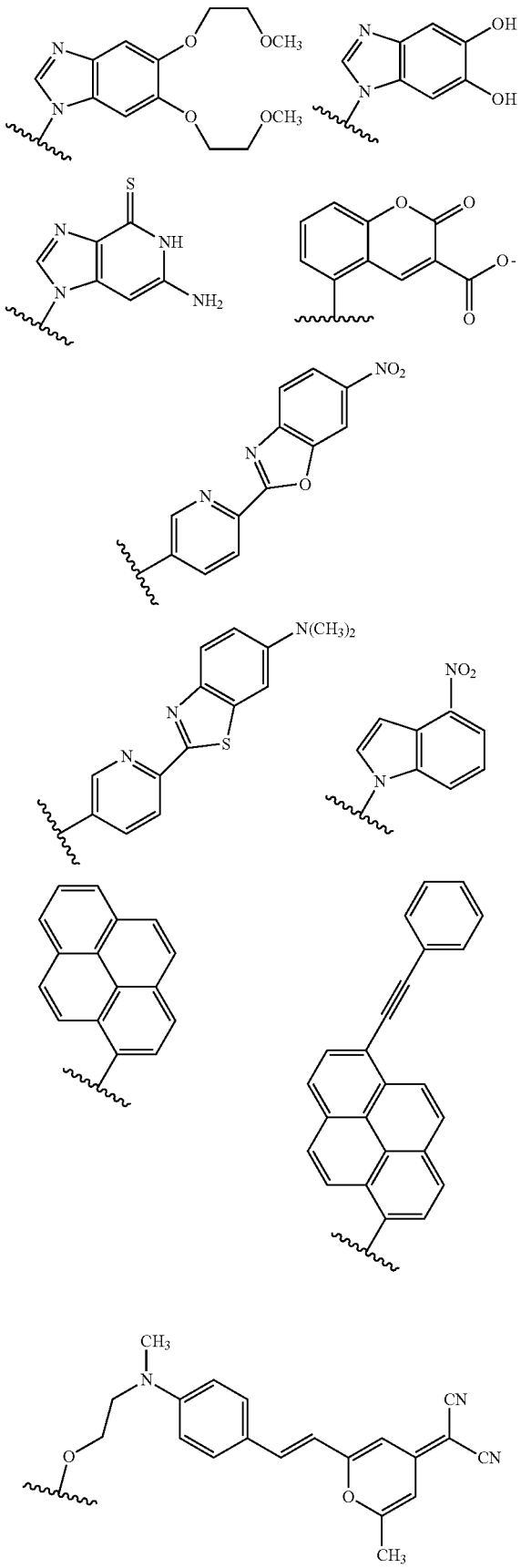

-continued

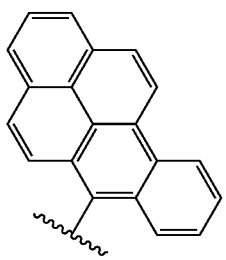
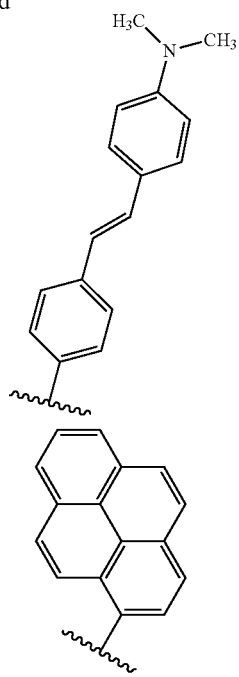
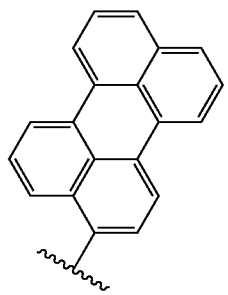
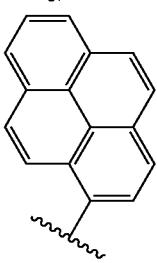
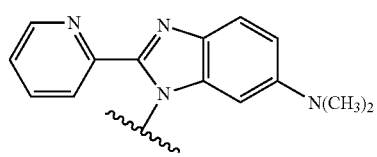
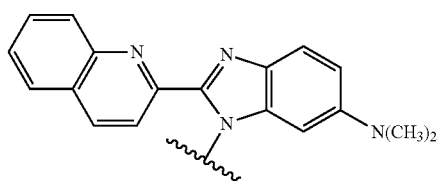
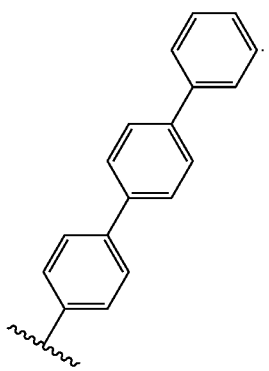

Due to the location of the fluorescent cyclic compound on the sugar moiety, the nucleoside analogs of the present invention may act as DNA or RNA base analogs. The subject nucleoside and nucleotide analogs may stack in an RNA or DNA helix.

In addition, a non-fluorescent nucleoside analog having a cyclic compound such as cyclohexane, cyclohexene, decalin, or benzene joined to a carbon atom of a sugar molecule, can be used in ODFs of the present invention. In some embodiments, the cyclic compound is joined to the C-1 position of a sugar moiety. In some embodiments, the sugar molecule is pentose, hexose, ribose or deoxyribose. Such a nucleoside analog is useful as a non-fluorescent spacer which may be inserted between the subject fluorescent nucleoside analogs and unlabeled nucleic acid bases. Insertion of the non-fluorescent nucleoside in an oligonucleotide or oligonucleotide analog limits quenching which may occur between fluorophores. In some embodiments, a non-fluorescent nucleoside analog spacer has no cyclic compound attached to the sugar molecule, i.e, the spacer is a pentose or hexose, such as ribose or deoxyribose. Other spacer monomers of interest include tetrahydrofuran spacer analog with hydrogen replacing the C1 oxygen of deoxyribose; a triethylene glycol linker in place of a sugar and a base; and dihydrothymidine. Spacers are useful for separating nucleotides from one another, changing the fluorescence interaction between fluorophors, adding negative charge and increasing solubility of oligomer, etc.

In accordance with the present invention, a subject nucleoside analog may be substituted at various positions on its ring structure with one or more alkoxy, alkylamino, dialkylamino, alkyl, alkenyl, alkynyl, hydroxy, or halide groups. Examples include but are not limited to methoxy, ethoxy, dimethylamino, diethylamino, nitro, methyl, cyano, carboxy, fluoro, chloro, bromo, iodo, or amino groups.

In some embodiments, a fluorophore, ligand, quencher or spacer compound is attached at any available position on its ring structure to the sugar moiety by a bond, e.g, a carbon-carbon, carbon-oxygen, or carbon-nitrogen bond, in a subject nucleoside analog. Both alpha and beta anomers of the subject nucleosides are contemplated by the present invention.

In one embodiment of the invention, a nucleoside analog has the following structure or the α-anomer isomer thereof, or a substituted version thereof:

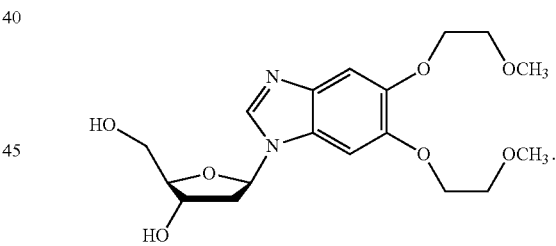

In another embodiment of the invention, a nucleoside analog has the following structure, or the α-anomer isomer thereof, or a substituted version thereof:

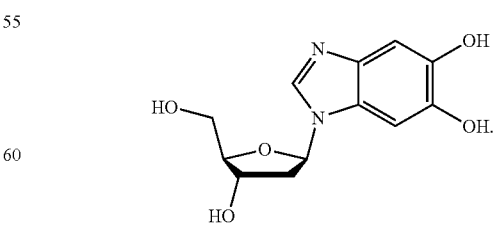

In another embodiment of the invention, a nucleoside analog has the following structure, or the α-anomer isomer thereof, or a substituted version thereof:

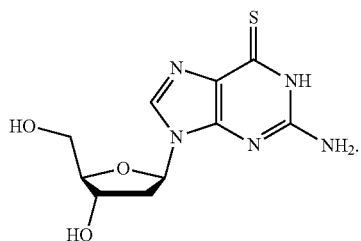

In another embodiment of the invention, a nucleoside analog has the following structure, or the α-anomer isomer thereof, or a substituted version thereof:

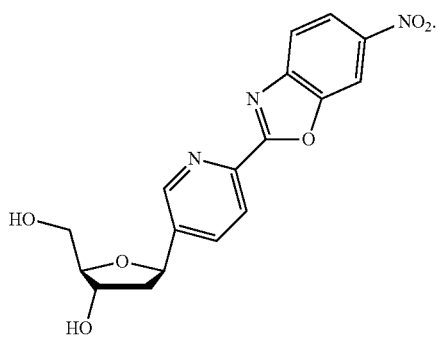

In another embodiment of the invention, a nucleoside analog has the following structure, or the α-anomer isomer thereof, or a substituted version thereof:

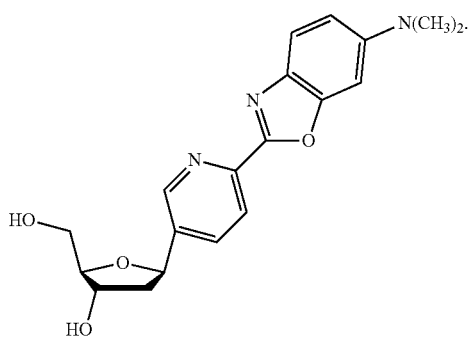

In another embodiment of the invention, a nucleoside analog has the following structure, or the α-anomer isomer thereof, or a substituted version thereof:

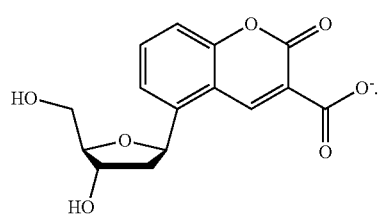

In another embodiment of the invention, a nucleoside analog has the following structure, or the α-anomer isomer thereof, or a substituted version thereof:

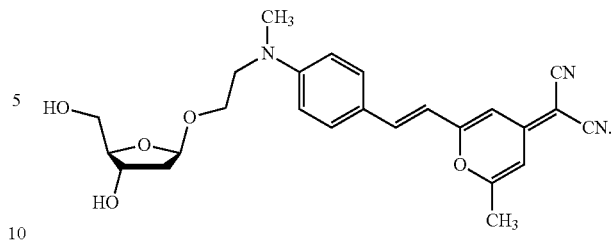

In another embodiment of the invention, a nucleoside analog has the following structure, or the α-anomer isomer thereof, or a substituted version thereof:

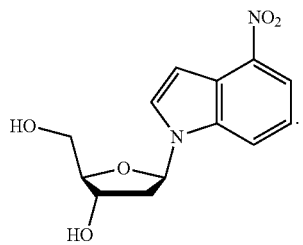

In another embodiment of the invention, a nucleoside analog has the following structure, or the α-anomer isomer thereof, or a substituted version thereof:

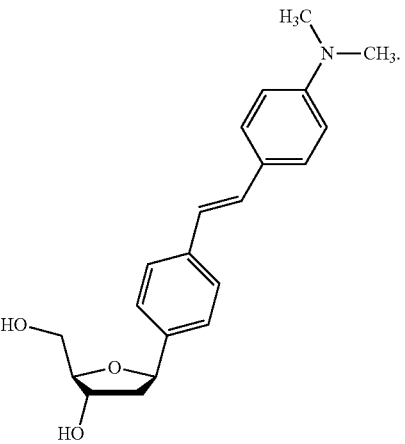

In another embodiment of the invention, a nucleoside analog has the following structure, or the α-anomer isomer thereof, or a substituted version thereof:

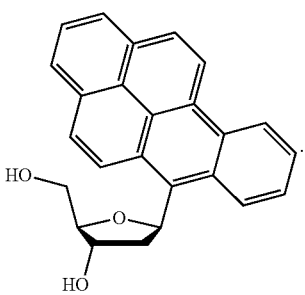

In another embodiment of the invention, a nucleoside analog has the following structure, or the α-anomer isomer thereof, or a substituted version thereof:

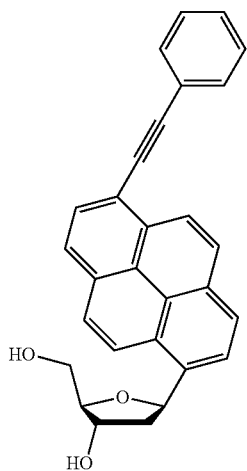

Useful intermediates provided by the present invention includes the nucleoside analog 5'-3'-paratoluoyl diesters.

Other useful intermediates provided by the present invention include, for example, the nucleoside analog 5'-dimethoxy trityl ethers.

Useful phosphoramidite derivatives provided by the present invention include N, N-diisopropyl-O-cyanoethyl phosphoramidite derivitized at the 3' alcohol of the subject nucleoside analogs.

The subject nucleoside analogs, when incorporated into an oligonucleotide or oligonucleotide analog, such as RNA or DNA, provide fluorescence at a range of from about 350 nm to about 1100 nm emission maxima.

The subject fluorescent nucleosides of the present invention can be synthesized by coupling a fluorescent cyclic compound to a sugar using a modification of the organocadmium strategy described in Schweitzer and Kool (1995) J. Am. Chem. Soc. 117:1863. The non-fluorescent spacer, ligand and quencher molecules may be made the same methodology. The disclosure of this article and of all other articles cited in this application are incorporated herein as if fully set forth.

The C-nucleoside coupling involves the reaction of organocadmium or organozinc derivatives of the cyclic species with the well known α-chlorosugar synthon of Hoffer (Hoffer, M., (1960) Chem. Ber. 93:2777). The glycosidic coupling of a cyclic compound to a sugar coupling results in a mixture of alpha and beta anomers in isolated yields of between about 54-81%. The primary product of this coupling reaction is the C1-coupled product formed with retention of configuration. Alpha-anomeric C-nucleotides are the primary reaction products. Although the alpha orientation is not the same as for natural beta nucleotides, alpha nucleosides are also known to form DNA-like helices and models indicate that they can still interact well with natural bases in neighboring positions.

Toluoyl protecting groups may be removed in methanolic base. Thus, in accordance with the present invention, free unprotected nucleosides can be produced in as little as two steps: cyclic coupling and ester deprotection. The alpha-anomers may be converted to the beta configuration by a third step, acid-catalyzed equilibration. A preferred acid catalyzed equilibration reaction uses benzenesulfonic acid in refluxing xylene, in the presence of a small amount of water.

The present invention also provides use of an oligomer of the subject nucleoside analogs which can be attached to generally any compound via a chemical bridge such as a thiol group. Methods for joining molecules can be found, for example, in S. L. Beaucage and R. P. Iyer (1993) Tetrahedron 49:1925-1963.

In addition, the present invention provides for oligonucleotide analogs in which fluorophore, ligand, spacer and quencher compounds replace some or all of the DNA or RNA bases. Natural oligonucleotides are strings of nucleosides bridged by phosphodiesters. Oligonucleotide analogs are oligonucleotides in which the structures of the bases, sugars, and/or phosphodiesters are modified, e.g., to change or enhance molecular properties.

A chemical structure of a fully fluorophore-substituted subject oligodeoxyfluoroside analog is provided below. In the structure depicted below, "fluorophore" is meant to encompass any of the subject nucleoside analogs described herein. In some embodiments, in the structure depicted below, "fluorophore" can be substituted at one or more positions by a ligand, spacer or quencher group. In some embodiments, the end hydroxyl groups are substituted with linkers, spacers, or quenchers.

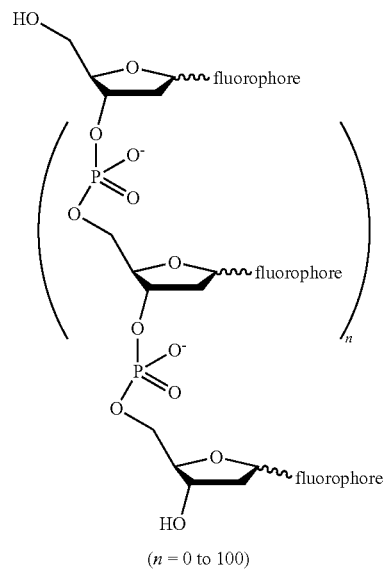

($n$ = 0 to 100)

The current invention provides oligonucleotide analogs where a base is replaced with a subject nucleoside analog, but also contemplates modifications in the sugar-phosphate backbones known to those familiar with the art. Examples of known oligonucleotide analogs in which the sugar or phosphate backbone is modified include phosphorothioate DNA, 2'-O-methyl RNA, phosphoramidate DNA, 2' fluoro DNA, peptide nucleic acid (PNA), and alpha-DNA. Thus, beyond using the natural DNA/RNA sugar-phosphate backbone, the present invention also contemplates oligonucleotide analogs having one or more of the bases replaced with fluorophores. The generalized structure for a PNA comprising the subject nucleoside analogs is shown below. In the structure depicted below, "fluorophore" is meant to encompass any of the nucleoside analogs of the present invention. In some embodiments, in the structure depicted below, "fluorophore" can be substituted at one or more positions by a ligand, spacer or quencher group.

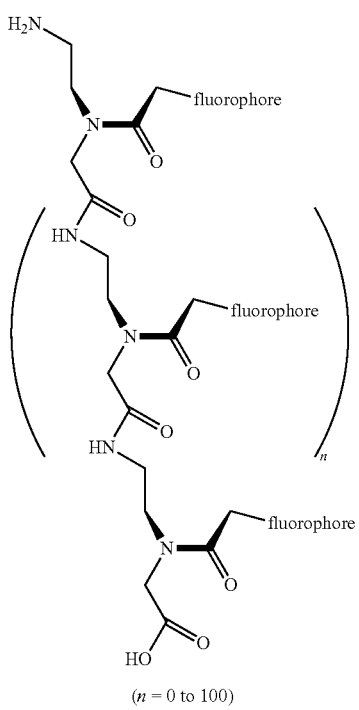

(n = 0 to 100)

The nucleoside analogs of the present invention may be incorporated into an oligonucleotide or oligonucleotide analog strand during synthesis by any of a myriad of procedures known for making DNA or RNA. For example, such procedures include enzymatic synthesis and chemical synthesis. Chemical synthesis includes solution or solid phase techniques.

Enzymatic methods of DNA oligonucleotide synthesis frequently employ Klenow, T7, T4, Taq or E. coli DNA polymerases as described in Sambrook et al. (1989, Molecular Cloning: A Laboratory Manual, Cold Spring Harbor Press, NY). Enzymatic methods of RNA oligonucleotide synthesis frequently employ SP6, T3, or T7 RNA polymerase as described in Sambrook et al. Reverse transcriptase can also be used to synthesize DNA from RNA (Sambrook et al.). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, linear oligonucleotides can be prepared by PCR techniques as described, for example, by Saiki et al., 1988, Science 239:487.

Chemical synthesis of linear oligonucleotides is well known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases in addition to the nucleoside base analogs of the present invention are incorporated into the oligonucleotide, and particularly if modified phosphodiester linkages are used, then the synthetic procedures are altered as needed according to known procedures. In this regard, Uhlmann et al. (1990, Chemical Reviews 90:543-584) provide references and outline procedures for making oligonucleotides with modified bases and modified phosphodiester linkages.

Synthetic oligonucleotides may be purified by polyacrylamide gel electrophoresis or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, J. Am. Chem. Soc. 104:976; Viari, et al., 1987, Biomed. Environ. Mass Spectrom. 14:83; Grotjahn, et al., 1982, Nuc. Acid. Res. 10:4671). Sequencing methods are also available for RNA oligonucleotides.

In some methods, DNA oligonucleotides are synthesized by automated methods using a DNA synthesizer and β-cyanoethylphosphoramidite chemistry. Extended coupling times (10 minute) are preferably used for the subject cyclic compound-derivatized nucleoside residues. Oligomers may be purified by preparative denaturing polyacrylamide gel electrophoresis and isolated by methods known in the art such as the crush and soak method.

The subject fluorescent nucleosides of the present invention can be incorporated into an oligonucleotide or oligonucleotide analog in order to achieve fluorescence labeling. Standard methods may be used to convert the unprotected nucleosides to 5'-dimethoxytrityl-protected derivatives. For example, the unprotected subject nucleosides may be co-evaporated with dry pyridine, then dissolved in pyridine and methylenechloride. A catalytic amount of DMAP, and both diisopropylethylamine and 4,4'-dimethoxytrityl (DMT) chloride is then added and the mixture stirred at room temperature for about eight hours. Hexanes are added and the mixture loaded on a flash silica gel column and the product, 5'-dimethoxytrityl-protected derivatives, eluted. These derivatives may then be converted into cyanoethyl phosphoramidite derivatives for incorporation into an oligonucleotide or oligonucleotide analog sequence.

The preparation of 3'-O-phosphoramidites from the 5'-dimethoxytrityl-protected cyclic compound-derivatized nucleosides is achieved by methods well known in the art such as, for example, dissolving the protected nucleoside derivatives in dry methylene chloride and adding diisopropylethylamine and 2-cyanoethyl N,N,-diisopropylchlorophosphoramidite. The reaction mixture is stirred at room temperature for a period of about 4 hours after which hexanes are added. The mixture is then loaded to a flash silica gel column and the product eluted as an oil.

In accordance with the present invention, one or more of the subject nucleoside analogs may be incorporated at various positions in an RNA or DNA sequence. For example, one or more subject nucleoside analogs may be incorporated within a stretch of sequence so that the DNA or RNA fragment is effectively tagged towards the middle of the molecule. One or more subject nucleoside analogs may also be incorporated near or at the end of an RNA or DNA sequence.

In another aspect of the invention, one or more of the subject nucleoside analogs may be incorporated within a linear nucleic acid molecule, or at either or both the 5' or 3' ends of a linear nucleic acid molecule. The subject fluorescent nucleosides may be present in more than one position in an RNA or DNA molecule. In some embodiments, at least two subject nucleosides are placed adjacent to one another within an RNA or DNA sequence. The RNA or DNA sequence may comprise a linear, hairpin, dumbbell, circular, or branched conformation and may be single or double stranded.

Useful properties of fluorophores include intense fluorescence (which depends on absorbance and quantum yield) and choices of multiple wavelengths of emission. The subject nucleoside analogs offer high absorbance and many possible wavelengths. Another property of fluorophores is a long Stokes shift as it helps avoid background fluorescence.

The fluorescently labeled nucleoside derivatives of the present invention are particularly useful when attached to a solid support such as controlled pore glass (cpg) or a polystyrene bead.

In another aspect of the invention, there are provided compositions and methodologies for constructing combinatorial arrays of fluorophores (CFAs) built on a oligonucleotide or oligonucleotide analog backbone. The combinatorial arrays are built from a library of the subject nucleoside analogs, hereinbefore described in detail. Other fluorescent nucleoside analogs such as pyrene, perylene, anthracene, phenanthrene, tetracene and pentacene-derivatized nucleosides described in U.S. Pat. Nos. 6,479,650 and 6,670193, may also be used in the CFAs of the present invention. Other nucleoside analogs including ligand and spacer and quencher groups may also be used in the CFAs of the present invention.

In one embodiment, a library is constructed on multiple solid supports such as Tentagel® beads using well known split-and-pool methods such as those described in Ohlmeyer M H et al. (1993) "Complex synthetic chemical libraries indexed with molecular tags." Proc Natl Acad Sci USA (90): 10922-10926.

Other supports which can be used to attach the nucleoside analogs include e.g., polystyrene, PMMA, polyacrylamide, cellulose, controlled pore glass, or geysen pins. Alternatively, arrays may be separated in space on one or more large solid supports. Examples of larger size supports include e.g., glass, microscope slides, micro titer dishes, and tea bags. In this embodiment, a final library of fluorophore arrays is produced in which each solid support from a collection of multiple solid supports, or each location on a large solid support, has attached thereto, only one type of oligomeric sequence comprising the subject fluorescent nucleoside analogs. The library is made up of many of such solid supports or locations on one or more large solid supports. Thus, members of the library may be different with respect to one another due to their individual nucleoside analog makeup. In some embodiments, only the subject nucleoside analogs are incorporated into an oligomer.

In some embodiments an oligomer of the present invention includes as little as about two subject nucleoside analogs and as many as about one hundred, such as about 2 to 20 nucleoside analogs, such as 2, 3, 4, 5, 6, 7, 8, 9, 10, 11, 12, 13, 14, 15, 16, 17, 18, 19 or 20 nucleoside analogs.

In some embodiments an oligomer of the present invention has a length of as little as 2 and as much as 100, such as a length of about 2 to 20, such as a length of about 2, 3, 4, 5, 6, 7, 8, 9, 10, 11, 12, 13, 14, 15, 16, 17, 18, 19 or 20.

Libraries of oligodeoxyfluorosides (ODF) sensors of the present invention can be prepared using combinatorial methods. In some embodiments the ODF libraries can be synthesized on PEG-polystyrene beads so that each bead has only one type of compound on it. In some embodiments the length of the ODF members of the library is 4, i.e., a tetramer, where 5-12 different monomer species can occupy any position of the sequence. For example, with 5 different monomers, a tetramer ODF can be prepared in $5^4$ combinations (625 different compounds). For example, with 11 monomers, a tetramer library can contain >14,000 different compounds.

In another embodiment, unlabeled, non-fluorescent nucleosides or nucleic acid sequences are added to the solid supports, either 5' or 3' to the subject nucleoside analogs or interspaced between the nucleoside analogs. In still another embodiment of the invention, one or more subject non-fluorescent nucleoside analogs (i.e., spacer molecules) such as e.g., cyclohexane-2-deoxyriboside, cyclohexene-2-deoxyriboside, decalin-2-deoxyriboside, or benzene-2-deoxyriboside, are interspaced between the fluorescent nucleoside analogs or between fluorescent nucleoside analogs and non-labeled nucleosides. The incorporation of one or more subject non-fluorescent nucleoside analogs, which act as spacer molecules, prevents quenching of fluorescence by the natural nucleoside bases.

Members of the library may be selected based on absorption and emission characteristics. Selection of beads with interesting and useful fluorescence characteristics is performed by fluorescence microscopy or the naked eye under ultraviolet light, transilluminator, or other forms of fluorescence imaging.

To aid in the identification of one or more desired members of a subject CFA library, the libraries may be encoded using the methods described in Ohlmeyer M. H., et al., (1993) "Complex synthetic chemical libraries indexed with molecular tags." Proc. Natl. Acad. Sci. USA 90:10922-10926. Identification of a sequence on a given bead is carried out by chemical treatment of the bead, followed by gas chromatography. If desired, the sequence may be made again on a preparative scale in order to better characterize it. Many other combinatorial deconvolution methods are known to those of skill in the art and may be used to help identify one or more members of the library.

The present invention also provides a method for selecting an oligofluor suitable for use as a sensor. The method comprises constructing a combinatorial fluorophore array library as described above and selecting a particular nucleoside analog or sequence of nucleoside analogs which emits the most intense fluorescence, or which emits a specific wavelength of light, or which exhibit the greatest change upon exposure to the analyte. Selection may be performed using fluorescence microscopy, naked eye under UV light, or transilluminator.

In yet another embodiment of the invention, there is provided a method for identifying a subject nucleoside analog which exhibits significant Stokes shifts. The method entails exciting a subject CFA library at a short wavelength and selecting one or more fluorophore arrays which emit at much longer wavelengths. The range of short wavelength useful for practicing this aspect of the invention is about 200 nm to about 1000 nm. Selection is done as described above.

In still another embodiment of the invention, a method for identifying a fluorophore sequence that changes its emission wavelength or intensity on binding an analyte is provided. The method comprises constructing a combinatorial fluorophore array library attached to the solid support(s), allowing an analyte solution to contact the library, and selecting library members that change emission wavelength intensity or wavelength on binding of the analyte molecule.

Methods of Detection

Analytes are detected by combining a sensor of the invention with a test sample suspected of comprising the analyte of interest. Where the analyte is present, it binds to the sensor, causing a change in the fluorescence. The change is fluorescence is detected by any convenient method, as known in the art. Reference samples of known analyte composition may be included in an assay, or used to establish reference curves. Typically positive and negative controls are included. Analytes of interest for analysis include, for example, metal ions, organic molecules in the gas or vapor state, and anions.

The test samples comprising analytes of interest may be provided in solution, vapor or gaseous state. A plurality of assays may be run in parallel with different analyte concentrations to obtain a differential response to the various concentrations. As known in the art, determining the effective concentration of an analyte typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the analyte or at or below the concentration of analyte that does not give a detectable change in fluorescence.

In some assays multiple analytes are simultaneously detected by multiple sensors where the fluorescence can be read with one light source and filter set.

A further embodiment of the invention is directed towards ODF sensors for the detection of toxic metals. For example a ODP library on beads can be synthesized and screened against metal ions, e.g., a set of 22 heavy/toxic metal cations (V3+, Cr3+, Mo3+, Mn2+, Os3+, Co3+, Ni2+, Cu2+, Ag+, Zn2+, Cd2+, Hg2+, Be2+, Ba2+, In3+, Tl+, Ge4+, Sn4+, Pb2+, As3+, Sb5+, Se4+), to identify and characterize sensors, and to develop a set of sensors on beads. Sensors can be characterized in terms of affinity and selectivity for various analytes of interest.

A further embodiment of the invention is directed towards ODF sensors for the detection of anions. For example, an ODF library on beads can be screened for responses in water to a set of toxic/EPA-listed anions (CN−, ClO4−, HPO42−, AsO33−, OCl−, NO2−, NO3−, BrO3−, SCN−, F−, N3−, SeO32−, CrO42−, MnO4−, BO033−, CH3CO2−, oxalate), where the ODF library can be pre-treated with one or more metal ions such that sensors include one or more metal ions bound to the oligomer. In some embodiments a set of sensors with known metal ion binding properties will be screened for responses in water to a set of anions of interest.

A further embodiment of the invention is directed towards ODF sensors for the detection of organic compounds. For example, screening of an ODF library for response to organics in the vapor phase. In some embodiments, binding of the analyte of interest in the vapor phase may involve hydrogen bonding (e.g., for analytes that have acidic protons or lone pairs); stacking (e.g., for analytes that contain flat π-systems); or electrostatics (e.g., for groups that may be attracted to the phosphate backone charge in the ODF). For example, screening of an ODF library can be performed to investigate responses to organic compounds of interest in aqueous solution (e.g., in an aqueous phosphate buffer). For compounds of interest that are sparingly soluble in water, a small amount of ethanol or DMF (e.g., 1-3%) can be added to the buffer to confer some solubility.

Some organic compounds of interest include: petroleum components and additives, such as decane, benzene, xylenes, PAHs (naphthalene, phenanthrene), MTBE and tetraethyl-lead; sulfur compounds found in oil, such as thiacyclopentane, 2-methylthiacyclohexane, thiophene and benzothiophene; cleaners/degreasers, monomers and solvents such as dichlorobenzene, ethylene dibromide, 111-trichloroethane, vinyl chloride, acrylonitrile, acrylamide, methylmethacrylate, styrene, bisphenol A, polychlorinated biphenyls, polychlorinated hydrocarbons; and pesticides and herbicides such as alachlor, atrazine, 2,4-D, glyphosate. In some embodiments, screening involves the selection of a minimal set of sensors on beads for pattern responses to organic compounds of interest.

EXPERIMENTAL

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

General Synthesis Methods

The previously described method of C-nucleoside coupling was utilized to generate the nucleoside analogs. The method involves cadmium- or zinc-mediated reaction of Grignard derivatives of cyclic compounds with Hoffer's chlorosugar. The primary product in this coupling reaction is the C1alpha-coupled product, formed with retention of configuration.

Solvents used as reaction media were purified and dried by distillation over $CaH_2$ (pyridine, MeCN and $CH_2Cl_2$), Na (THF) or MeONa (MeOH) before use. Chemicals were purchased from Acros, Aldrich, Alfa-Aesar, Lancaster, Fisher, or J. T. Baker. Flash chromatography (FC): silica gel MeMerck 60, 0.040-0.063 mm. $^1$H-NMR (400 MHz) and $^{13}$C-NMR (100 MHz) in $CDCl_3$ unless otherwise stated; chemical shifts in ppm rel. to TMS, coupling constants J in Hz.

General Procedure A

A solution of the arylbromide in dry THF was slowly added to Mg-turnings in dry THF. To start the Grignard reaction, a few drops of 1,2-dibromoethane were added and the mixture was slightly heated. After complete addition of the arylbromide solution, the reaction mixture was stirred for 2 h at 50° C. $CdCl_2$ was then added and the mixture was stirred for 2 h at reflux. The reaction was cooled to room temperature and a solution of the Hoffer's chlorosugar in THF was added. After stirring for 16 hours at room temperature, the solvent was evaporated, the residue was suspended in $CH_2Cl_2$ and washed twice with 10% NH4Cl soln. The aqueous layers were extracted with $CH_2Cl_2$ and the organic layers were dried (MgSO4) and concentrated. Purification by FC (hexanes/EtOAc 6:1) gave the pure alpha-anomers (the beta-anomers as minor products were not isolated).

General Procedure B

Freshly prepared 0.5 M $NaOCH_3$ in MeOH was added to a solution of the protected nucleoside in MeOH/$CH_2Cl_2$ 1:1. After stirring for 4 hours at room temperature, crystalline NH4Cl was added and the solvent was evaporated. Purification by FC (EtOAc) gave the pure deprotected nucleosides.

General Procedure C

The deprotected nucleoside was coevaporated twice with pyridine and then dissolved in pyridine/$CH_2Cl_2$ DMT-Cl, DIEA and a catalytic amount of DMAP were added and the reaction mixture was stirred for 4-8 hours at room temperature. The solvents were then evaporated and the residue was purified by FC (hexanes/EtOAc 4:1-1.5:1, preequilibrated with hexanes containing 5% TEA).

General Procedure D

2-Cyanoethyl N,N-diisopropylchlorophosphoramidite and DIEA were added to a solution of the DMT-protected nucleoside in $CH_2Cl_2$ and the mixture was stirred for 5 hours at room temperature. The solvent was evaporated and the residue was purified by FC (hexanes/EtOAc 3:1, preequilibrated with hexanes/EtOAc 3:1 containing 5% TEA)

Example 2

Preparation and Screening of a Library for Metal Sensors

Libraries of oligodeoxyfluorosides (ODF) sensors are prepared using combinatorial methods; they are produced on PEG-polystyrene beads. ODF libraries are prepared so that each bead has only one type of compound on it. A typical length is a tetramer, where 5-12 different monomer species can occupy any position. For example, with 5 different monomers, a tetramer ODF can be built in $5^4$ combinations (625 different compounds). With 11 monomers, a tetramer library can contain >14,000 different compounds.

A library of tetrameric ODFs was synthesized on a DNA synthesizer on PEG-polystyrene beads from nucleoside phosphoramidite monomers based on the following structures:

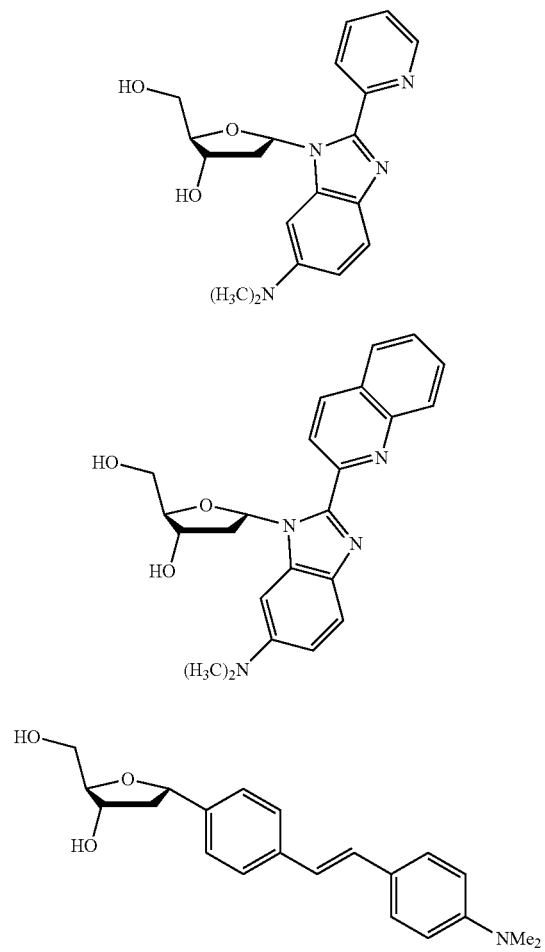

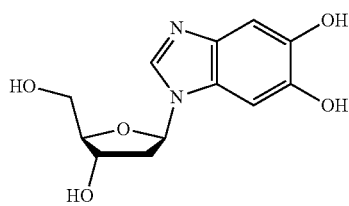

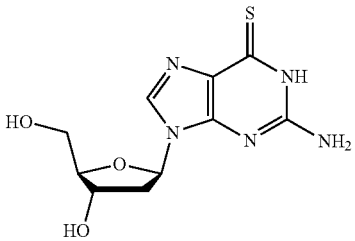

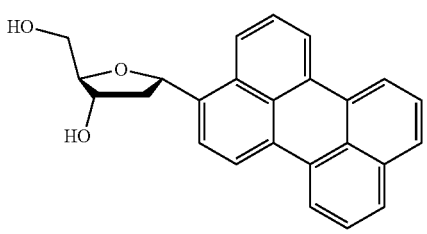

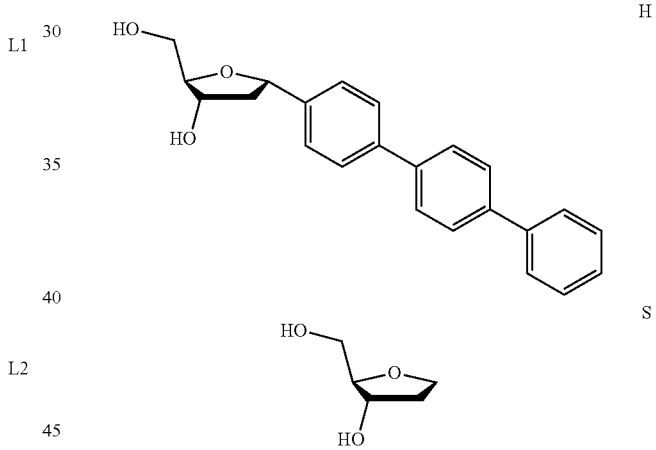

Figure 4:
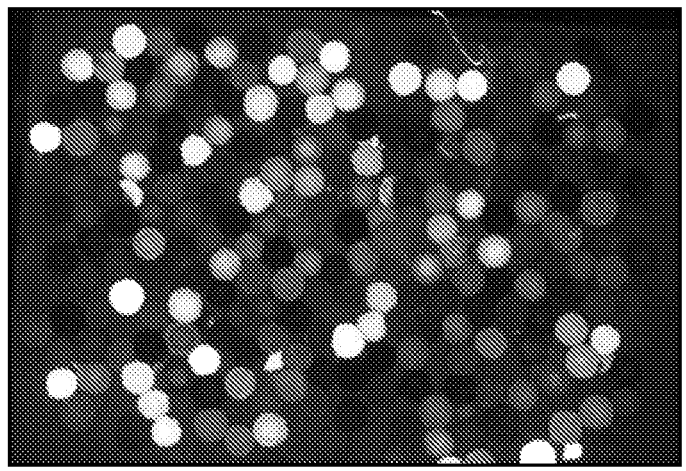
FIG. 4 illustrates images of a library during a' screening procedure. Top is beads with ODF sensors on them (one sequence per bead). After exposing to the analyte metal ion (middle image), a difference image is made (bottom), revealing those ODFs that respond strongly to the metal ion. Colors represent color shifts, while changes in intensity correspond to lighting up or quenching. 50% gray represents no change.
Figure 4:
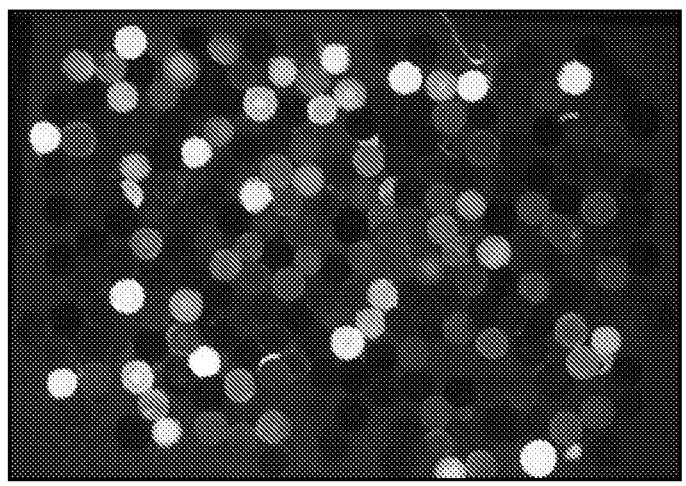
Figure 4:
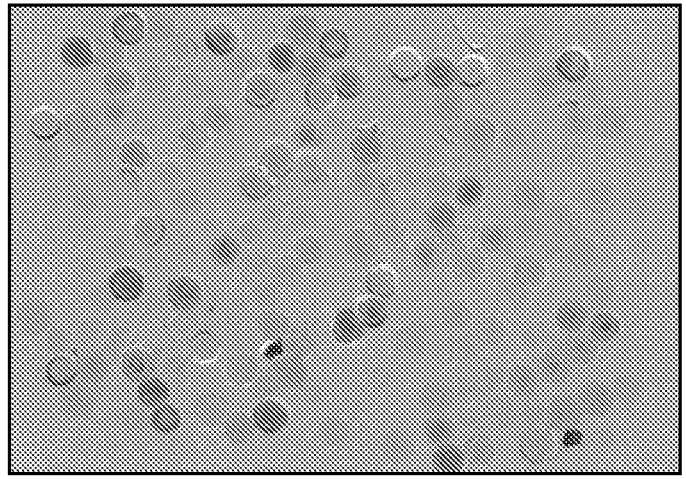

FIG. 4 illustrates the library screening results. Top image shows beads with ODF sensors on them (one sequence per bead). The middle image shows the beads after exposing the beads to the analyte metal ion. The bottom image shows a difference image, revealing those ODF beads that respond strongly to the metal ion. Colors represent color shifts, while changes in intensity correspond to lighting up or quenching, and 50% gray represents no change.

Examples of ODF Sensors Found by this Screening Method

Figure 5:
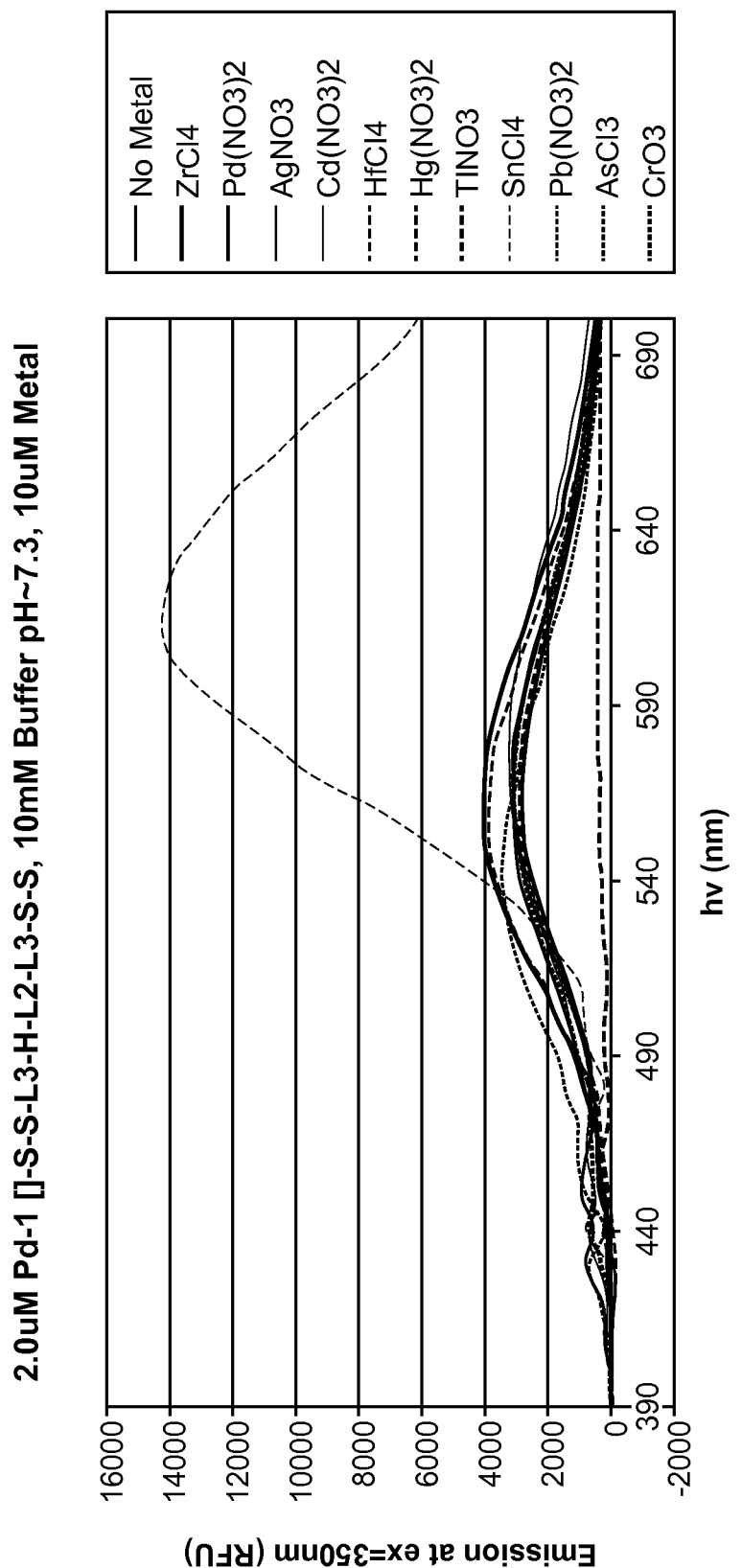
FIG. 5 illustrates the fluorescence emission response of a sensor to various metal ions.

Silver ion sensor: Sequence 5'-S-S-L3-H-L2-L3-S-S-3' (note: 2 "S" residues were added at each end to increase water solubility and decrease aggregation tendency) sensed $Ag^+$ at 2 micromolar in aqueous solution with a strong light-up signal at 615 nm. No signal was seen from $Zr^{4+}$, $Pd^{2+}$, $Cd2^+$, $Hf^{4+}$, $Hg^{2+}$, $Tl^+$, $Sn^{4+}$, $Pb^{2+}$, $As^{3+}$, $Zn^{2+}$, $Cu^{2+}$, $Ni^{2+}$, $Fe^{3+}$, $Cr^{3+}$ or $Mn^{2+}$. FIG. 5 shows the fluorescence emission response of the sensor to 10 uM of various metal ions. Although ligands L2 and L3 are likely to bind many metals, it only yields a positive signal for silver. The results show that this specific sensor sequence yields a selective electronic interaction with silver ions in a non-obvious way.

Figure 6:
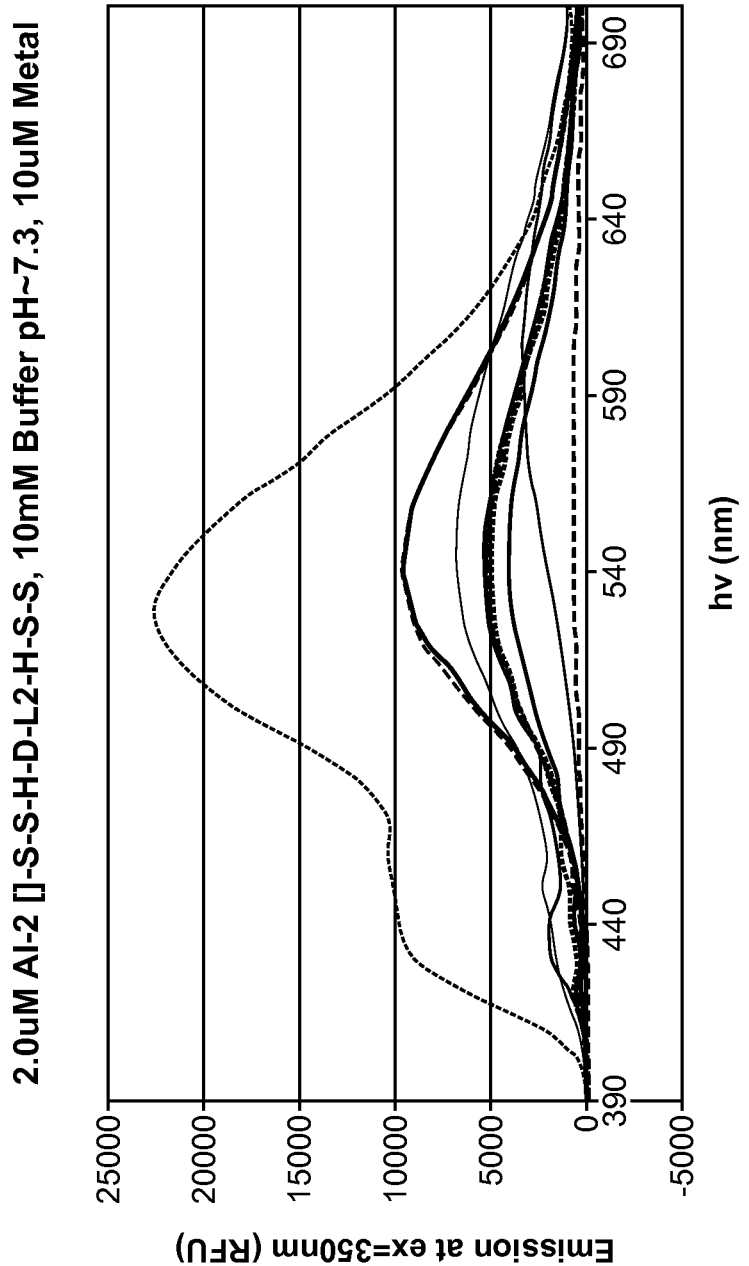
FIG. 6 illustrates the fluorescence emission response of a sensor to various metal ions.

Lead sensor: Sequence 5'-S-S-H-D-L2-H-S-S-3' sensed Pb²⁺ at 2 micromolar in aqueous solution with a strong light-up signal at 615 nm. No signal was seen from $Zr^{4+}$, $Ag^+$, $Pd^{2+}$, $Cd^{2+}$, $He^+$, $Hg^{2+}$, $Tl^+$, $Sn^{4+}$, $As^{3+}$, $Zn^{2+}$, $Cu^{2+}$, $Ni^{2+}$, $Fe^{3+}$, $Cr^{3+}$. FIG. 6 shows the fluorescence emission response of the sensor to 10 uM of various metal ions. Although this ODF sequence also contains ligand L2 and monomer H (like the silver sensor), it yields a selective response for lead. Although ligand L2 likely can bind multiple metals, the electronic interactions in this sequence yield a selective signal.

Example 3

A library of ODF tetramers on PEG-PS beads was constructed using nucleoside phosphoramidite monomers based on the following structures:

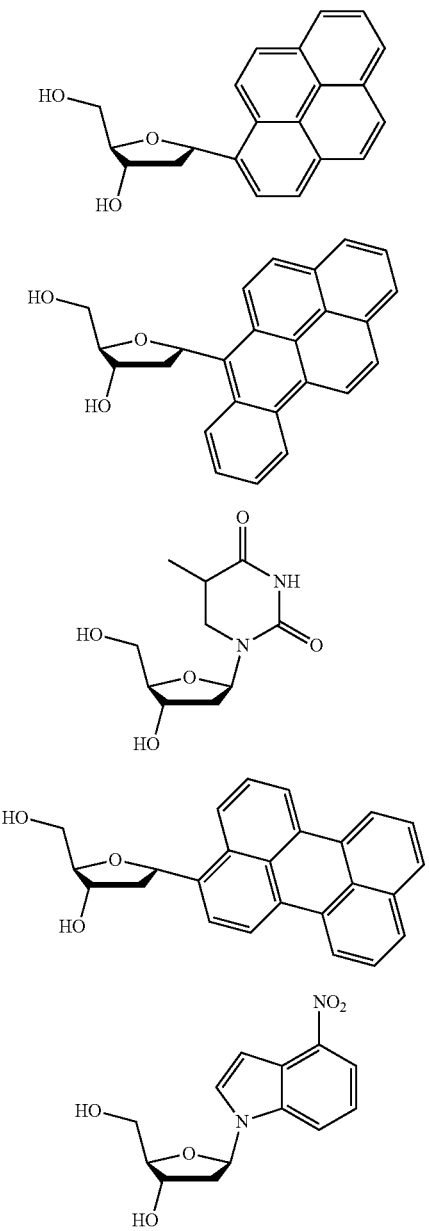
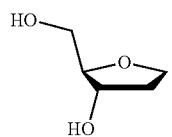
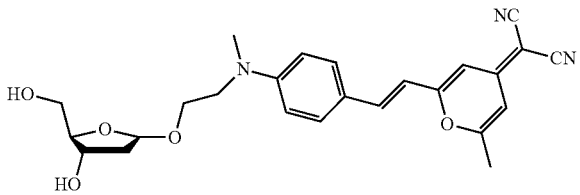

The library was screened for ODFs that change fluorescence upon exposure to organic vapors. Images were taken before and after exposure, and a difference image was constructed before.

The following examples in Table 1 show sensor sequences identified for a number of analyte vapors given below. See FIG. 7 for images of the sensor beads during screening. Note that many of the sequences contain similar components; although they respond to different analytes. This shows that the ability respond by a fluorescence change is non-obvious and not necessarily predictable a priori. Moreover, the mechanism of binding a specific analyte is not yet known and not immediately obvious. In addition, the physical mechanism for yielding a quenching or color change response is not yet known. These sensors can be used directly on the beads, or they can be synthesized as pure molecules in solution, and deposited on a solid surface (paper, plastic, glass) for sensing. These sensors can be used individually, one sensor per analyte, or in combinations to give a pattern of responses.

TABLE 1

| | Sensors to organic compound vapors | | |
|---|---|---|---|
| Entry | Analyte | Beads | Sequences: 5'→3' |
| 1 | Acrolein | FS-1 | DHT-I-E-DHT |
| | | FS-2 | Y-E-DHT-DHT |
| 2 | Methyl iodide | FS-4 | E-DHT-S-E |
| | | ES-5 | Y-S-Y-K |
| 3 | Acrylonitrile | FS-9 | S-Y-Y-E |
| 4 | Ethyl isocyanate | FS-15 | Y-DHT-Y-DHT |
| 5 | Mesitylene | FS-17 | Y-Y-S-B |
| | | FS-18 | Y-E-B-Y |
| 6 | Propionic acid | FS-19 | Y-DHT-B-S |
| | | FS-21 | S-DHT-E-S |
| 7 | Nitrobenzene | FS-24 | Y-S-E-S |
| | | FS-25 | Y-Y-E-K |
| 8 | dimethylaniline | FS-26 | Y-E-B-I |
| | | FS-27 | S-E-B-DHT |

Example 4

Synthesis of an ODF Library

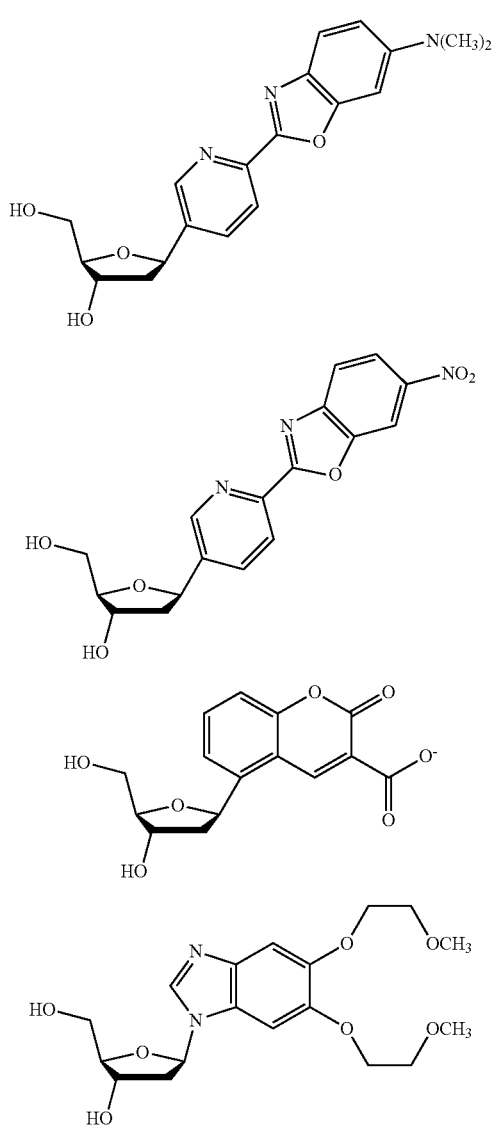

An ODF library can be prepared, by standard methods, to include two nitrogen-rich ligands (L1, L2) with good chemical stability (with respect to loss of ligand from the sugar) under the conditions of metal ion binding and the acidic conditions of DNA synthesis, and two oxygen-rich ligands for oxophilic metals (L3 and L4). Other deoxyfluoroside monomers, for example, a 6-thioguanine monomer, a terphenyl spacer and a basic spacer, and perylene and pyrene monomers can also be used in the synthesis of the library. A total of 8-9 monomers, yields a tetramer library of 4096-6561 compounds on beads.

Screen with a Set of 20 Heavy/Toxic Metal Cations.

The library of potential metal ion sensors can be screened for responses to metal ions. Rather than screening blindly for all possible cations, a focused set of 22 ions that have high relevance to environmental contamination, to human health (because of toxicity), and relevance to the petroleum industry are selected. These are $V^{3+}$, $Cr^{3+}$, $Mo^{3+}$, $Mn^{2+}$, $Os^{3+}$, $Co^{3+}$, $Ni^{2+}$, $Cu^{2+}$, $Ag^+$, $Zn^{2+}$, $Cd^{2+}$, $Hg^{2+}$, $Be^{2+}$, $Ba^{2+}$, $In^{3+}$, $Tl^+$, $Ge^{4+}$, $Sn^{4+}$, $Pb^{2+}$, $As^{3+}$, $Sb^{5+}$, $Se^{4+}$.

The method of screening: Spread a subset of ODFs thinly in a field of view under the microscope in a non-chelating buffer (20 mM collidine.HCl, or HEPES, pH 7). Add the metal of interest (as a chloride or nitrate salt) at 10 µM, wait for equilibration, then re-image. Digital subtraction reveals beads that respond with color changes, increases or decreases in emission. The strongest responders are picked out physically and then sequenced by electron capture GC. Sequences of greatest interest and response can then be prepared in preparative quantities on the DNA synthesizer for studies in solution.

Characterize sensors in solution: Select 2-4 candidates for each ion and resynthesize them for characterization. The molecules are purified by HPLC and confirmed for composition by mass spectrometry. Evaluate fluorescence responses to the metal of interest as well as to the full set of ions. For the best sensors, perform titrations to measure binding affinity and threshold of sensitivity.

Develop a minimal set of sensors on beads: In some cases when screening for a large set of metals, the identified ODF sensors are not perfectly selective. For example, they may yield a "light up" enhancement signal for the metal of interest, but also yield a light up at a different wavelength for other metals, and quenching or wavelength shifts for others. By looking at the full set of metals and sensors, it is possible to find a small subset of ODFs that respond differently (taken as a pattern) for nearly every metal of interest. Select such a subset for the set of metals of interest. In some cases, a set of 4-6 ODFs should be sufficient for a selective pattern response to 20 analytes. By resynthesizing these compounds on beads, and using the responses on beads to read the pattern, selectivity can be tested. Although these sensors could be used as a group in solution, direct visual readout on beads may be simpler. For example, testing patterns can be done by placing the 4-6 beads on glass slides and exposing them to each of the metals separately. This should provide a full set of 20 individual patterns. Visual recognition of these patterns can be tested by providing blinded specimens of metals to identify.

Differential screening: In some cases, screening for a select subset (e.g., 10) of the above metals can be achieved in the following way: (a) image a specific group of beads in the library in the presence of 10 uM metal X along with the other 9 metals; (b) image the same group of beads in the presence of the other 9 metals (omitting X); (c) digitally subtract one image from the other. This will reveal single beads that respond to metal X differently than the 9 other metals. For example, for a limited set of 10 metals, 1-2 selective responder ODFs may be isolated and identified. Their selectivity of response can then be studied and characterized in solution.

Abbreviations

DIEA=N,N-diisopropylethylamine, DMAP=4-dimethylaminopyridine, DMT=4,4'-dimethoxytrityl, EtOAc=ethyl acetate, MeCN=acetonitrile, PdCl2(dppf)2=[1,1'-bis(diphenylphosphino)ferrocene]dichloropalladium(II), TEA=triethylamine.

Example 5

Polyfluorophores on a DNA Backbone: Sensors of Small Molecules in the Vapor Phase Vapors of small molecules are under widespread study in natural signalling, environmental monitoring, industrial quality control, and in medicine. In the last few decades, advances in chemistry and material science have enabled the development of chemical sensors of such volatile organics, in which conjugated polymers and cross-reactive chemical sensor arrays are the most widespread sensor types. Among them, optical vapor sensing arrays based on luminescence (including fluorescence) and absorbance have become essential. In the recent past, colorimetric detection of volatile organics using cross-reactive chemical sensors have been demonstrated in multiple applications.

Although absorbance-based methods for vapor detection have shown good success, fluorescence-based methods may offer some advantages, such as high sensitivity and low background. For example, the detection of vapors of nitroaromatics with conjugated polymers and bio-polymers has showed very high sensitivity. However, much of the power of fluorescence-based detection still remains unharnessed, since most current approaches involve the use of only one type or a few types of sensor molecules, resulting in a limited diversity of sensing (i.e., quenching). Additionally, in most current approaches the difficulty of synthesis of a set of sensor molecules and the lack of flexibility in conjugating them to supports can restrict their general utility.

Sensor molecules built by assembling multiple fluorophores on a DNA backbone could address some of these limitations. Such DNA-like oligomers can be synthesized rapidly in widely varied sequences and lengths on an automated instrument, and the iterative synthesis makes the preparation of large combinatorial libraries straightforward. In addition, the resulting oligomers are water-soluble and are readily conjugated both to small molecules and to solid supports. Most importantly for sensing, such oligodeoxyfluorosides (ODFs) undergo multiple forms of electronic interactions among the closely spaced chromophores, resulting in complex fluorescence emission properties that are quite distinct from the component monomers. We considered the possibility that interaction with a small molecule analyte might well alter such electronic interactions selectively, resulting in changes in emission, including quenching, but also possibly enhancement and/or shifts in wavelength as well.

Figure 8:
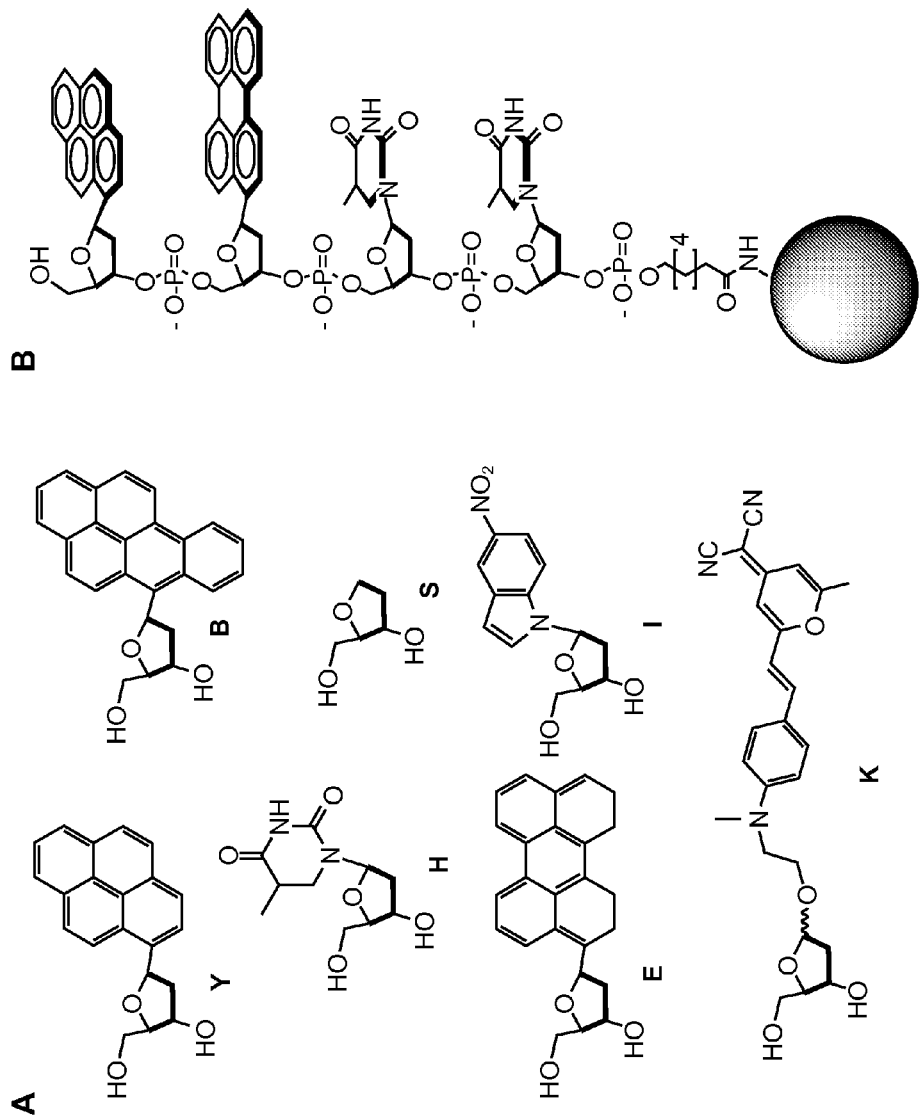
FIG. 8. A) Fluorescent and non-fluorescent monomers employed as components of the library; B) Example of sensor (5'-Y-E-H-H-3'), attached by an amide linkage to a PEG-PS bead.

To test this possibility, we constructed a library of 2401 tetramer ODFs conjugated to PEG-polystyrene beads by a stable amide linkage. Standard split-and-pool methods yielded a library in which each bead contained one specific tetramer structure. The sensor candidates were constructed in all possible sequences of seven monomer deoxyribosides (FIG. 8); these included four fluorophores (Y, E, B, K), a potential quencher (I), an abasic spacer (S), and a spacer/hydrogen bonding element (dihydrothymidine, H). Sequences were encoded by the tagging method of Still, readable on the single bead level by electron-capture GC.

Our initial qualitative tests of sensing capabilities among library members were directed to four vapors of four distinct small molecules. Acrolein (an example of an unsaturated aldehyde), mesitylene (electron-rich aromatic), propionic acid (aliphatic carboxylic acid) and nitrobenzene (π-electron-poor aromatic) were selected to represent diverse structural and electronic properties. A closed chamber was designed using quartz fluorescence cell in which beads from the library were placed onto a small microscope slide. The beads were exposed to one adjacent drop (4 µL) of analyte inside the cell, which was then capped. Fluorescence was monitored under an epifluorescence microscope using excitation 340-380 nm and observing all visible emission (long-pass filter, >400 nm). Images were taken before and after 2 min, 7 min, and 30 min of exposure to the vapor in the quartz chamber at 23° C.

To analyze possible changes in emission in response to analytes, we first constructed graphical 50% gray-based difference maps of the beads by inverting color/intensity of the image before exposure (i.e. making a photonegative) and merging it with the image taken after 30 min of exposure using 50% transparency (see Table 1 and details in SI). This difference image enables an easy visualization of the effect of the small-molecule vapor on the library of tetramers. Any part of the image that is 50% gray (including background and beads) indicates no change, while beads that are darker than 50% gray background reveal quenching, brighter beads show emission enhancement, and colors reflect a combination of the original ODF emission color and any wavelength shifts that occur on sensing. We secondly In addition to this, for selected sequences we determined a quantitative color change profile, a 3-dimensional vector ($\Delta R, \Delta G, \Delta B$), by substracting the RGB values of the image before exposure from the r, g, b values of the image after exposure. The color color-change maps were then analyzed by chemometric and statistical methods.

TABLE 2

Summary of cross-screening results, listing ODF sequences and their qualitative responses to analyte vapors (as shown by actual blended difference images of beads containing sensor molecules).

| Entry | Sensor Sequences | AC[a] | MS[b] | PA[c] | NB[d] |
|---|---|---|---|---|---|
| 1 | 5'-H-I-E-H | ● | ● | ● | ● |
| 2 | 5'-Y-E-H-H | ● | ● | ● | ● |
| 3 | 5'-S-S-Y-E | ● | ● | ● | ● |
| 4 | 5'-Y-Y-S-B | ● | ● | ● | ● |
| 5 | 5'-S-H-E-S | ● | ● | ● | ● |
| 6 | 5'-B-K-H-H | ● | ● | ● | ● |
| 7 | 5'-Y-S-E-S | ● | ● | ● | ● |
| 8 | 5'-Y-Y-E-K | ● | ● | ● | ● |

[a]Acrolein [b]Mesitylene [c]Propionic Acid [d]Nitrobenzene.

During screening we observed marked fluorescence responses for many of the ODF library members upon exposure to analytes, as indicated by color-shifted beads in the difference map. Two strongly-responding examples for each analyte were therefore selected, resynthesized, characterized by MALDI-MS, measured for absorption and emission spectra, and retested for sensing responses on beads. All beads reproduced the trends observed during the screening process with the exception of sequence 2; in this case it is possible that we mistakenly picked up a different bead than the one that was observed in the difference image. However, even this sequence showed good sensing properties that were distinct from the other sensor ODFs (Table 2).

While the selected sequences were able to detect the analytes they were chosen for quite clearly, we wished to see whether there was selectivity: did a given ODF respond the same to its selected analyte as to the other analytes? To answer this question we performed a cross-screening study of all eight ODF sequences against the four small molecules. The qualitative results are shown in Table 1. Importantly, most of the sensors showed widely varied responses to the four vapors, establishing that differences in sequence and monomer composition affect the responses markedly. Interestingly, sequences selected for their responses to individual analytes demonstrated (in the majority of cases) fluorescence responses to the other three analytes as well. Importantly, few responses were differents. Of the eight different sequences there were two or three distinct response patterns to the four analytes such, as exemplified by sequences 2, 4, and 7. For example, 5'-Y-H-E-HE-H-H (2) gave a blue shift for acrolein and a violet bright maroon difference image for nitrobenzene (Table 2). In contrast, 5'-Y-Y-S-B (4) gave a marked red difference response and a light brown response for these same two analytes respectively. In addition Notably, the data showed multiple clear cases of wavelength shifts in emission rather than simple quenching. Examples include 5'-Y-E-H-H (2), whose green emission shifts to turquoise upon exposure to acrolein, and 5'-S-H-E-S (5), which switches from green to cyan emission in the presence of propionic acid.

Figure 9:
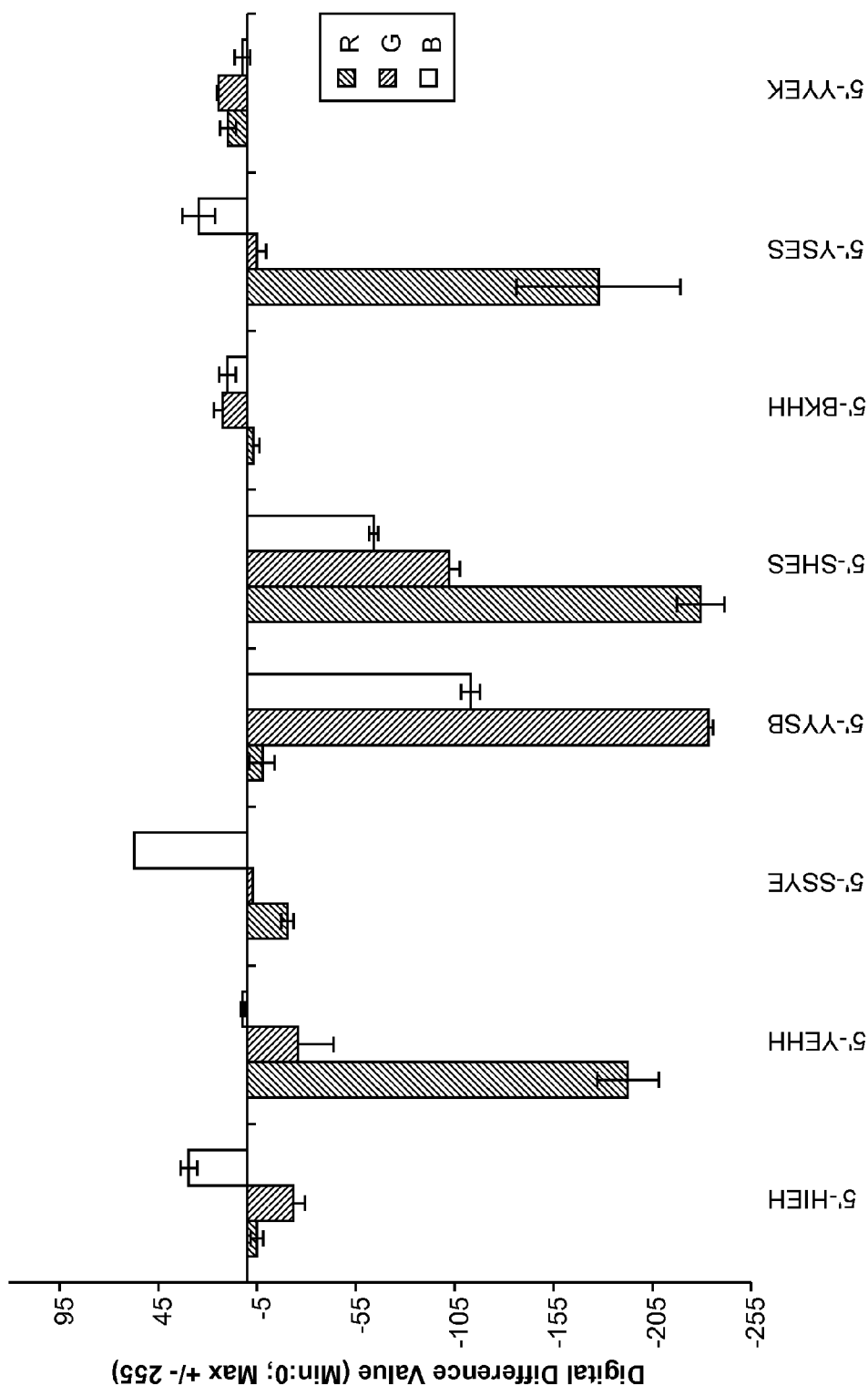
FIG. 9. Quantitative color change profile of sensor sequences upon exposure to acrolein.

The responses and reproducibility were further investigated quantitatively using the RGB color change profiles. The color change plots (FIG. 9) reflected the multiple strong responses observed, including those for of the sequences 2, 4, and 7. Indeed, recognition patterns were observed even for sequences that differed by only one component. Thus, 5'-Y-E-H-H (2) and 5'-Y-S-E-S (7) exhibited a strong red and a slight green quenching upon exposure to acrolein, while the blue wavelengths remained unchanged or slightly increased upon exposure to acrolein. Notably, these sequences contain the same two chromophores, and differ only in non-fluorescent components. Sequence 5'-S-H-E-S (5) showed a plain decrease of all three RGB values with acrolein, while and 5'-Y-Y-S-B (4) exhibited mainly a green and blue quenching. The same tetramers showed a relative quenching in response of mesitylene vapors, but with a different pattern and a stronger general quenching in presence of nitrobenzene vapors. Interestingly, in the presence of propionic acid vapors, an increase in the blue and green channels is observed for (1), (3), and (6) s, and red and green for (8), demonstrating "light up" responses in those cases.

Figure 10:
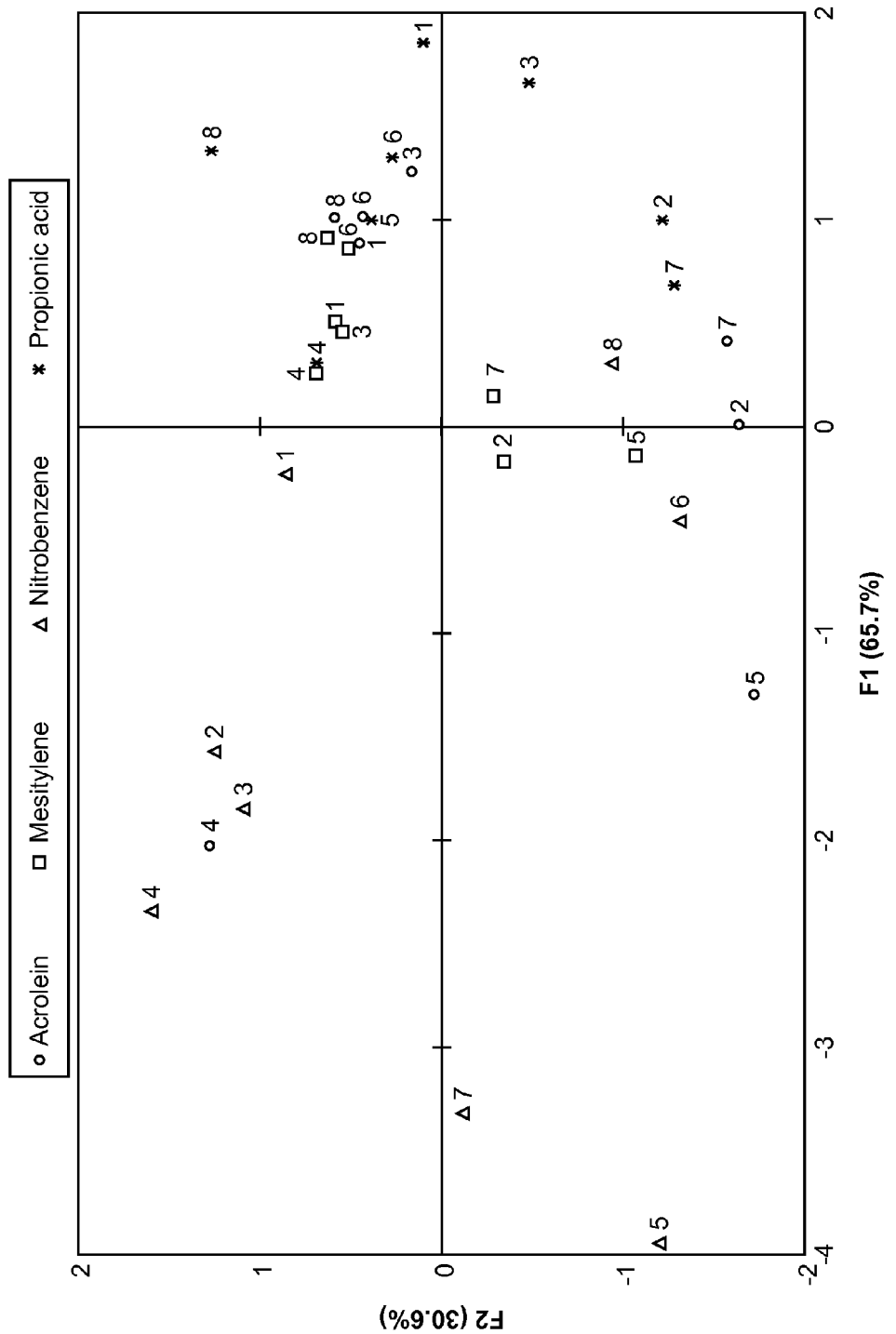
FIG. 10. Principal component analysis plot of ODF sensor responses upon exposure to the four analytes. Sensors 1-8 are listed in Table 2 and are shown by number here, with colors denoting the analyte for each data point. Each data point represents an average from 5-6 sensor beads.

To better understand the relationships in the data, we performed principal component analysis (PCA) on the full cross-screening data as shown (in FIG. 10). The first component F1 accounts for 65.7% of variance and the second component F2 accounts for 30.6%. The sum of the variances is equal to 96.3%. Thus, two main clusters of sensor behavior are revealed. Within clusters, similarities are observed. One is centered along the first component axis and the other cluster is centered along the second component axis. Sequences within a cluster act either similarly or weakly upon exposure to the analytes. Interestingly, the observations related to data for acrolein and nitrobenzene vapors, show the best largest spread in component values. For example, the responses of 5'-S-H-E-S (5), 5'-Y-Y-S-B (4), and 5'-Y-Y-E-K (8) are really very well separated in the presence of nitrobenzene vapors. The score plot of those sequences upon exposure to acrolein and mesitylene also produces a good separation. Their pattern responses in the presence of propionic acid are similar to one another but very distinct from the patterns for the other three analytes. Notably, the difference images (Table 2) and color change profiles showed that even a single sensor could be used to distinguish between the four analytes (sensor 5 for example).

In addition, the hierarchical cluster analysis approach (HCA) analysis was performed, which provides providing clusters of sensor responses tetramers by using the single linkage method. The clustering scheme is based on the squared Euclidean distance between the centroids of the clusters of sensor response. The data generated a dendrogram in which classes of tetramers can be identified based on their pattern responses. The quantitative PCA and AHC methods taken together allowed us to select a small set of distinct sensors that could be used in a pattern response for these analytes. The dendogram shows the pattern similarities of the color change profiles of sequences. Thus both methods revealed quantitatively the pattern responses of tetramers. More importantly, using these analytic methods, a combination of three sequences sensor molecules, such as 5'-S-H-E-S (5), 5'-Y-Y-S-B (4), and 5'-Y-Y-E-K (8), was shown to clearly discriminate the four analyte vapors with greater confidence than a single sensor.

The results show clearly that ODFs on beads can act as selective fluorescence sensors of a range of chemically distinct organic analytes in the vapor phase. We hypothesize that the varied responses arise from distinct electronic interactions between the analytes and each ODF, which has its own sequence-based electronic interactions initially.

Also of interest is the mechanism of association between the analyte molecules and the ODFs. We note that some but not all of the observed responses were reversible upon opening the chamber to air, implicating weak noncovalent attractions in some cases but possibly stronger bonds in others. Possible noncovalent contributions may include hydrogen bonding to the dihydrothymidine monomer (present in half of the selected sensors), electrostatic attractions to the phosphate anion backbone and its counterion, and/or van der Waals/stacking interactions with the large aromatic chromophores. It is also possible that the PEG-PS bead itself helps absorb and concentrate the vapor near the sensors; some bead swelling was noted with selected analytes.

Overall, the results are significant on multiple counts. First, they establish that oligomeric fluorophores can behave as vapor sensors with varied responses beyond simple quenching, which has been the only main response observed to date in most previous fluorescent gas-phase sensors. Second, the data show sequence-based responses that are distinct for multiple classes of analytes, thus broadening fluorescent vapor sensing far beyond detection of simple nitroaromatics. Third, the described library-based synthesis and screening approach enables facile evaluation of thousands of potential sensors for many analytes, rather than the previous one-at-a-time approach. Finally, the ODF sensor molecules are rapidly and easily synthesized in automated fashion using a small set of monomer components.

Example 6

Differentiating Between Fluorescence-Quenching Metal Ions with Polyfluorophore Sensors Built on a DNA Backbone The detection and identification of heavy metals in aqueous solution is broadly important to environmental monitoring and biomedical science. Many methods have been used to detect metal ions including fluorescence spectroscopy, UV-vis absorption, atomic absorption, ICP emission spectroscopy, and voltammetry. Among these methods, fluorescence spectroscopy is an attractive approach because of its high sensitivity, facile operation, and the widespread availability of equipment for analysis. As a result, fluorescent sensor molecules have been developed for many metals, in some cases yielding highly selective signals at low concentrations.

One of the problems faced in detecting metal ions with fluorescent sensors is the emission-suppressing effects of some metal ions, which results in strong quenching of fluorescence. Inherently quenching metal ions such as $Hg^{2+}$, $Cu^{2+}$, $Co^{2+}$, $Ni^{2+}$, and $Fe^{3+}$ can interfere with the fluorescent signal of the sensors in detecting other metals. Moreover, this quenching tendency makes it difficult to design a sensor that yields a positive (turn-on) signal. Indeed, the inherent ability of these metal ions to quench fluorescence has been exploited in some cases to develop turn-off sensors. However, in many applications it is not ideal to monitor the disappearance of a signal because fluorescence quenching can be caused by a number of factors, and therefore can be nonspecific. For higher sensitivity, it is usually desirable to have sensors that yield an enhancement of signal upon binding metal ions.

A second problem with the quenching tendency of such metals is that it is difficult to differentiate between metals that all typically yield a strong quenching response. To address problems such as these, a number of strategies have been employed to develop turn-on fluorescent sensors for quenching metals, such as separating the ligand moiety from the chromophore via rigid linker; the use of PET, FRET or excimer formation; or exploiting the specific reactivity of a given metal ion. Even with these advances, it is difficult with one approach to differentiate between a broad set of heavy transition metals.

An alternative strategy that has been used to differentiate heavy metal ions is that of sensor arrays. Sensor arrays commonly use a set of fluorescent indicators/sensors to discriminate a number of metal ions, and the pattern of responses as a whole is diagnostic of a given metal. Recent reports have used fluorescent polymers or common commercial dyes, with or without competing ligands, to distinguish between different transition metals. In such cases the fluorescence changes have been limited to quenching or enhancement, without changing wavelengths of emission. This limited response can add a requirement for more complex sensing schemes or signal processing that involves time-dependent parameters (such as dual lifetime referencing, time before color change, or time for color change halfway point). A small diversity of responses can also lead to the need for a larger number of sensors to distinguish even a relatively small set of analytes. Moreover, some of these prior sensors exhibit limited water solubility, requiring the use of organic or mixed solvents.

To address these challenges, we have adopted a new molecular approach to fluorescence sensors that incorporates fluorophores and metal ligands onto DNA-like oligomers (oligodeoxyfluorosides, or ODFs). This design allows the binding and reporting moieties to interact intimately by bringing them into direct contact by π-π (stacking, analogous to the stacking of DNA bases. Our hypothesis is that the signal transduction of this system should not be limited to a single mechanism, such as the commonly used PET, but rather can involve many mechanisms, offering a diversity of possible responses to even strongly quenching metals. Here we have examined the feasibility of this design strategy by generating a set of water-soluble fluorescent sensors that can respond distinctly to different heavy metal ions in solution using a single excitation wavelength. We describe the differentiation of a set of eight typically quenching metal ions ($Co^{2+}$, $Ni^{2+}$, $Cu^{2+}$, $Hg^{2+}$, $Pb^{2+}$, $Ag^+$, $Cr^{3+}$, and $Fe^{3+}$) based on the diverse spectral responses of a few sensors developed by this approach as a proof of principle. We find that the sensors offer a wide variety of responses beyond simple quenching with these metals, including enhancements and red- and blue-shifts, and we identify a minimal set of two sensors that can be used as a group to differentiate the eight metal ions in solution.

Figure 11:
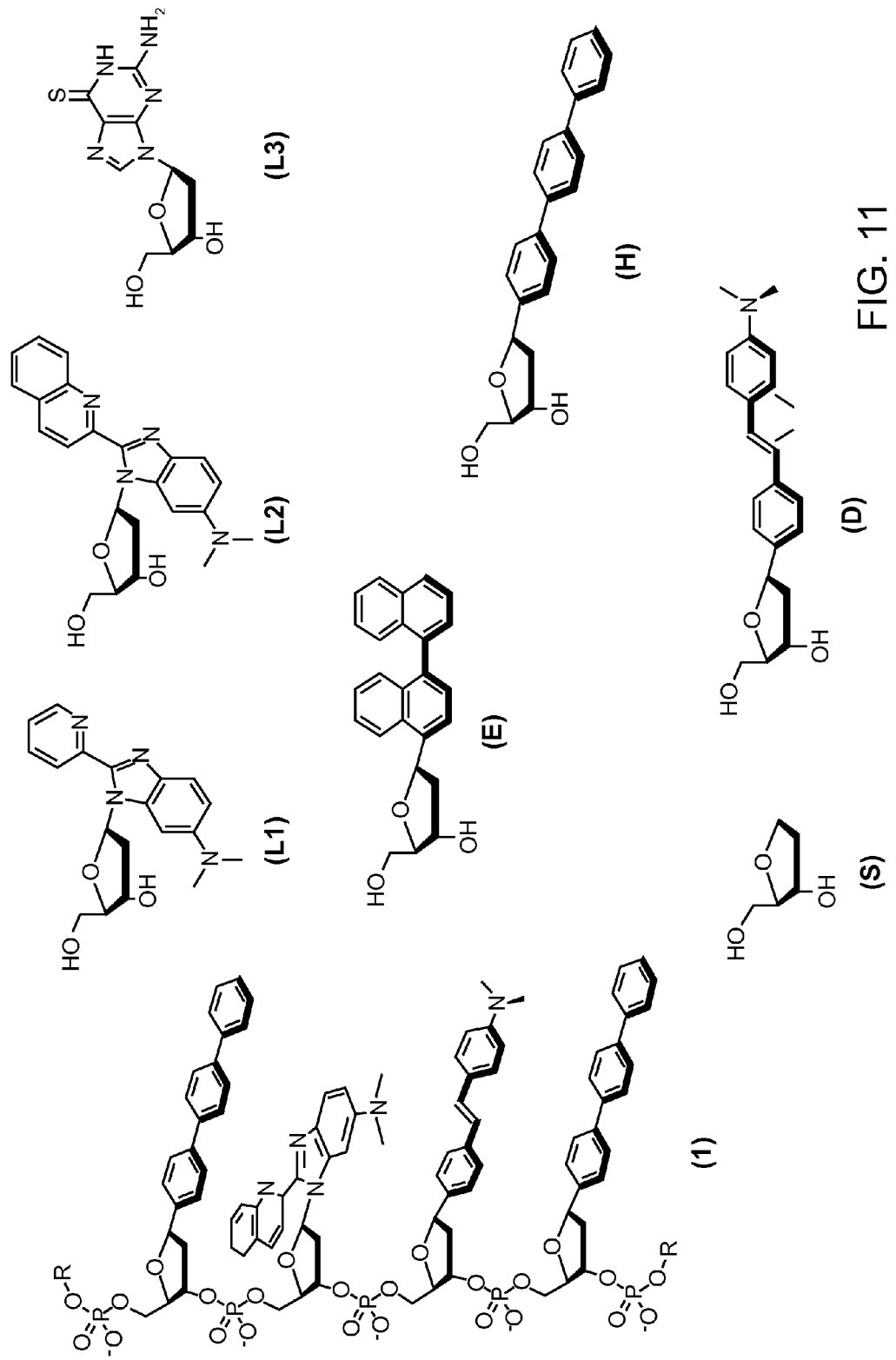
FIG. 11. Structures of an ODF sensor (oligomer 1, sequence H-L2-D-H, is shown as an example) and structures of the deoxyriboside monomers employed as components of the sensors. R=two tetrahydrofuran abasic spacer monomers.

Sensor Design. The current sensor design (FIG. 11) is based on a DNA-like structure of tetramer length, in which DNA bases are replaced by fluorophores and aromatic ligands. This oligodeoxyfluoroside (ODF) design is based on an expectation of strong inter-fluorophore electronic interactions encouraged by the DNA backbone. Fluorescent ligand deoxyribosides (L1, L2, and L3) were incorporated to add metal binding capacity and interact with fluorescent hydrocarbon fluorophores (E, H, and D) on the ODF. Upon binding, a metal ion is expected to alter the inter-fluorophore interactions within an ODF, significantly changing its photophysical properties. The ligands (L1, L2, and L3) were intentionally chosen to be non-selective for any specific metal in order to allow the ODFs to bind multiple metal ions. It was anticipated that any selective responses of a sensor for a particular metal would likely result not from the specificity of the ligands, but rather from the selective electronic interactions of ligands and neighboring dyes upon metal complexation, resulting in distinct signals for the different metal ions.

An advantage of this design strategy is that the sensors generated are not limited to a single sensing mechanism (e.g., PET). The design simply enables the fluorophores and ligands to interact on the DNA backbone, which can potentially generate sensors with different sensing mechanisms, offering a diversity of possible responses to various metal ions. Moreover, the phosphodiester scaffold allows for water solubility, and the modular nature of the ODF-based design enables rapid synthesis via automated synthesizer, and facilitates discovery of sensors from libraries.

Library Preparation and Screening. Because it is difficult to predict which ODF sequences would give the optimum signal for a wide variety of metal ions, a combinatorial library employing the split-and-pool method was prepared. The sensor molecules 1-6 studied here (Table 3) were identified from a screen of a library of tetrameric fluorophores and ligands on modified PEG-polystyrene beads synthesized on a DNA synthesizer. The library was prepared and screened by previously described methods, and contained six monomers (L1, L2, L3, E, H, and D) and a spacer (S). Two monomers (L3 and S, FIG. 1) were commercially available; fluorescent ligands L1 and L2, and fluorophore E, H, and D were synthesized as previously reported.

TABLE 3

Oligodeoxyfluoroside Sequences[a]

| Oligomer | Sequence |
|---|---|
| 1 | 5'-S-S-H-L2-D-H-S-S-3' |
| 2 | 5'-S-S-E-L1-E-S-S---3' |
| 3 | 5'-S-S-L1-L2-H-D-S-S-3' |
| 4 | 5'-S-S-L3-L2-H-L1-S-S-3' |
| 5 | 5'-S-S-L1-H-H-L3-S-S-3' |
| 6 | 5'-S-S-L1-S-L2-D-S-S-3' |

[a]Note that all sequences contain a phosphate group at the 3' terminus.

Figure 12:
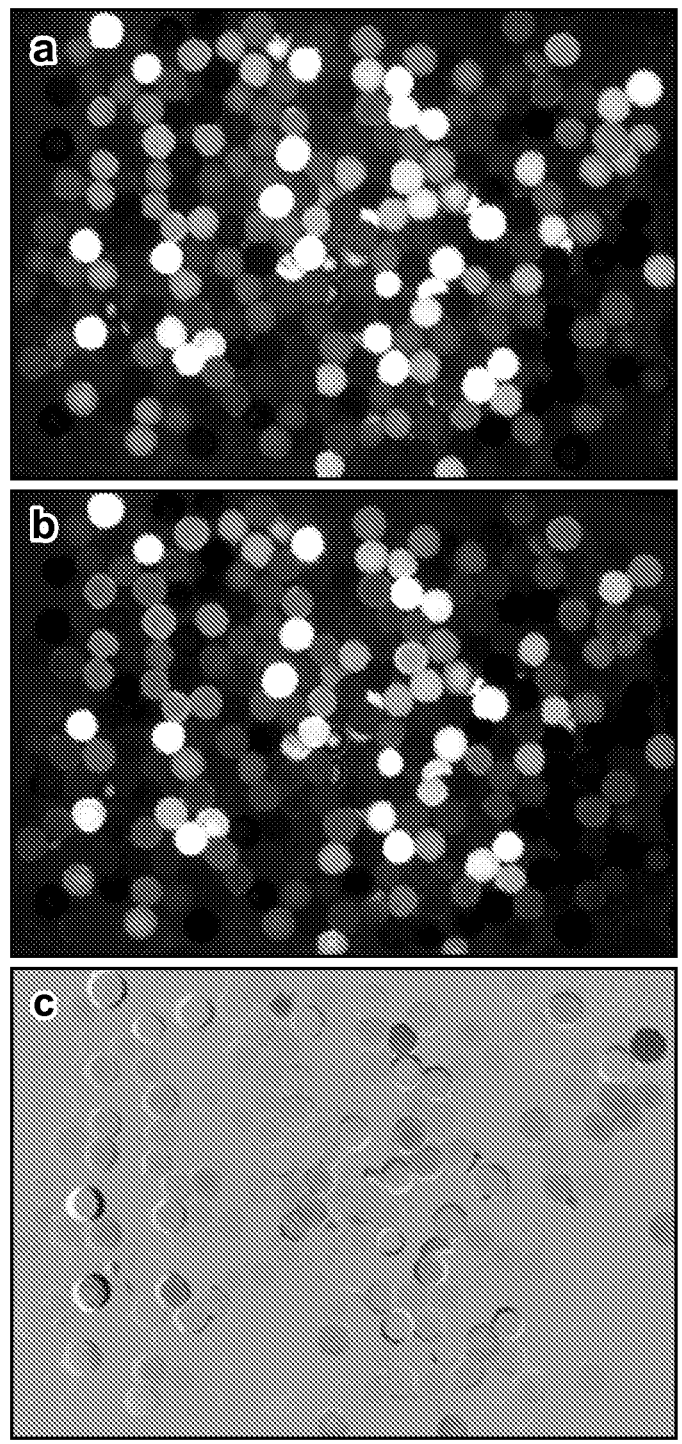
FIG. 12. Examples of images from library screening for fluorescence responses. (a) Library in buffer alone and (b) in the presence of 100 μM $AgNO_3$. To facilitate finding beads exhibiting fluorescence changes, image (a) was inverted and combined with (b) (50% blending) to produce difference image (c). In this difference image, 50% gray represents no change, while beads that are darker or lighter than gray show quenching and enhancement, respectively. Colors represent a combination of the original colors and the spectral shifts.

The beads were screened by imaging in buffer alone and then in the presence of 100 μM of each metal ($Co^{2+}$, $Ni^{2+}$, $Cu^{2+}$, $Hg^{2+}$, $Pb^{2+}$, $Ag^+$, $Cr^{3+}$, and $Fe^{3+}$). Beads exhibiting the strongest fluorescence change in the presence of each metal were selected and resynthesized for evaluation (FIG. 12). This led to identification of oligomers 1-6, which exhibited a variety of strong responses to this set of metal ions (see below). Although the sensing molecules were discovered as tetramers, additional abasic spacer nucleotide monomers (S), were incorporated on both ends of the oligomer in order to increase aqueous solubility, prevent aggregation, and facilitate purification for the solution studies. Unlike the nucleoside monomers (L1, L2, L3, E, H, and D), which are not appreciably soluble in water alone, oligomers 1-6 are functional in wholly aqueous media (see below).

Figure 13:
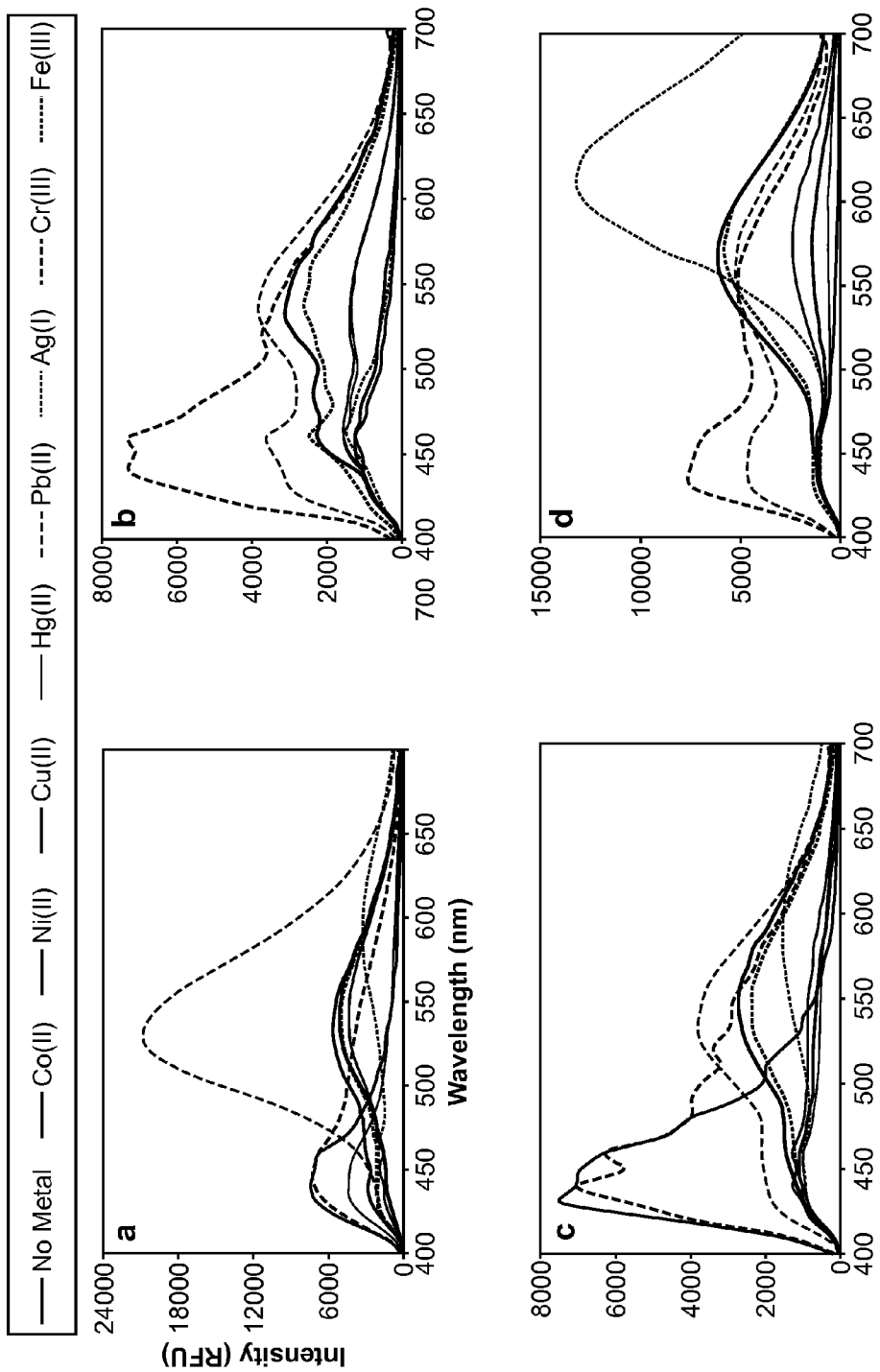
FIG. 13. Fluorescence response profiles of oligomers 1-6 (2 μM) to the quenching metal ions (10 μM) in 10 mM sym-collidine/$HNO_3$ pH ~7.3 buffer ($\lambda_{ex.}$=350 nm). (a)-(f) correspond to oligomers 1-6 respectively.
Figure 13:
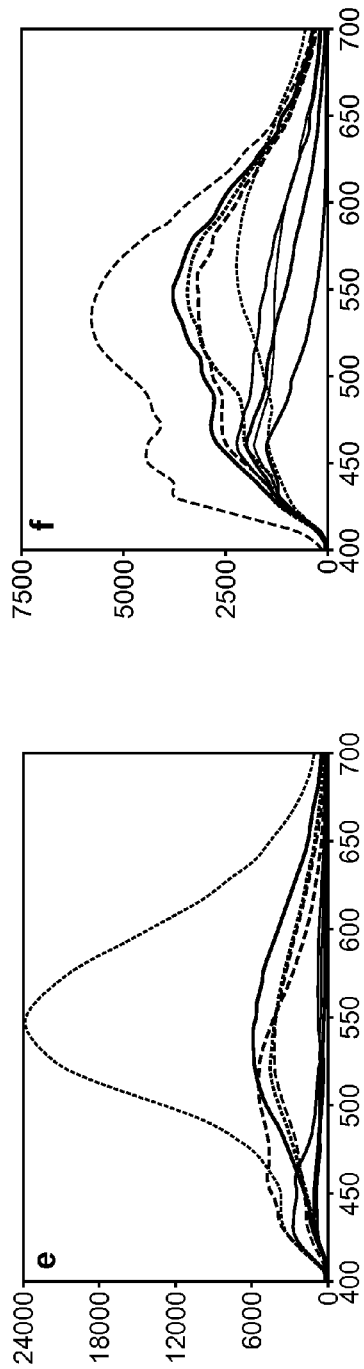

Metal Ion Discrimination. Oligomers 1-6 were characterized by MALDI mass spectrometry and their fluorescence spectra. In the absence of metal ions, the emission spectra of the six compounds appeared quite similar, with broad emission from ~420-670 nm, peaking at 530-570 nm. To evaluate metal ion responses, fluorescence spectra were measured in 10 mM sym-collidine.$HNO_3$ pH 7.3 buffer with 10 µM metal (as the nitrate salt). All six sensors were cross-tested against all eight metal ions. Spectra before and after addition are shown in FIG. 13, and the difference spectra profiles for each metal were plotted.

Synthesis and Purification. 5'-O-DMTr-protected 3'-2-cyanoethyl phosphoramidite derivatives of L1, L2, D, H and E were prepared according to references 1 and 2. 5'-β-DMTr-protected 3'-2-cyanoethyl phosphoramidite derivatives of L3 and S were purchased from Glen Research. These building blocks were directly used on a DNA synthesizer (ABI 394 DNA/RNA synthesizer). The oligomers were synthesized on a 1.0 µmole scale (3' phosphate CPG column, Glen Research) using the standard (DMT off) protocol but with extended (999s) coupling times for L1, L2 D, H, and E. Stepwise coupling yields were >90% as determined by trityl monitoring. Cleavage and deprotection of the oligonucleotide followed the recommended protocol for the 3' phosphate CPG column and L3 as indicated by Glen Research. The crude product was purified by HPLC (Jupiter 5u C5 column, 300 A, 250×10 mm, 5 micron) using TEAA, pH ~7.2 and MeCN as the solvent system. The oligomers were characterized by MALDI-MS (Table S1), and the absorption and fluorescence spectra of the purified oligomers are shown in FIG. 5i.

TABLE 3A

MALDI-MS Data for Oligodeoxyfluoroside Sequences[a]

| oligomer | sequence | calculated | found |
|---|---|---|---|
| 1 | 5'-S-S-H-L2-D-H-S-S-3' | 2422.6 | 2423 |
| 2 | 5'-S-S-E-L1-E-S-S-3' | 2015.4 | 2015 |
| 3 | 5'-S-S-L1-L2-H-D-S-S-3' | 2430.6 | 2431 |
| 4 | 5'-S-S-L3-L2-H-L1-S-S-3' | 2374.5 | 2376 |
| 5 | 5'-S-S-L1-H-H-L3-S-S-3' | 2316.5 | 2318 |
| 6 | 5*-S-S-L1-S-L2-D-S-S-3' | 2202.5 | 2203 |

[a]All Sequences contain a phosphate group at the 3' terminus.

Figure 14:
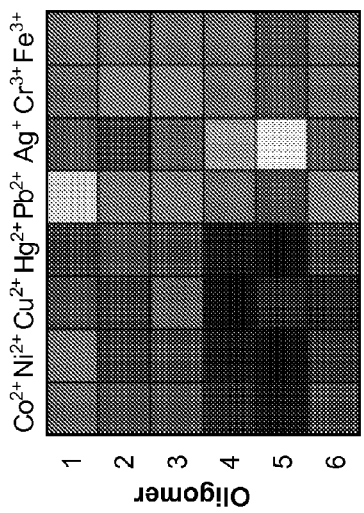
FIG. 14. RGB color representation of the changes in fluorescence response of sensors 1-6 to each of the eight metal ions. The three wavelengths selected to represent RGB are 650, 550, and 450 nm respectively. The fluorescence change values for each of the wavelengths were transformed into a 0-255 scale with 127 set as the value for no change. Thus, a metal inducing no fluorescence change is represented by a gray color (reference B). References A, B, and C represent RGB values of 0, 0, 0; 127, 127, 127; and 255, 255, 255.

To aid in visualization of the 48 spectral changes arising from the combinations of sensors and metals, we also prepared an RGB grid plot of all the sensors' responses to the eight metal ions (FIG. 14). The difference spectra data was condensed by selecting three wavelengths representing red, green, and blue and plotting them on a 256-unit RGB scale. The fluorescence changes were normalized into a 0-255 scale, with 127 set as the zero value. On this scale, fluorescence enhancement at the chosen RGB wavelength is represented by values greater than 127, with the maximum at 255; and fluorescence quenching is represented by values less than 127, with the strongest quenching value at 0. In the plot (FIG. 14), 50% gray represents no change either in emission intensity or color, while changes in intensity and wavelength are represented by light/dark values and colors, respectively.

Comparisons of Metal Responses. Examination of the fluorescence spectra of the oligomeric sensors in the presence of various quenching metal ions revealed a variety of responses in the sensors (FIG. 13). None of the metals yielded simple quenching with every sensor; aside from the characteristic fluorescence quenching, other responses induced by the metal ions included fluorescence enhancements, blue- and red-shifts, and spectral broadening due to the appearance of a new emission peak. For example, oligomer 3 responded strongly to all of the metals in the set except for $Fe^{3+}$. $Cr^{3+}$ broadened the spectrum of 3 by the appearance of a new peak at about 450 nm. $Cu^{2+}$ induced a blue-shift of ca. 100 nm in 3, while $Ag^+$ induced a red-shift of ~50 nm. $Co^{2+}$, $Ni^{2+}$, and $Hg^{2+}$ quenched the fluorescence of 3. Every sensor showed a light-up response with at least one of the metals.

Among the six sensors, ODF 1 displayed the most varied responses to the set of quenching metal ions. This is readily seen in FIG. 14 (top row) and also in FIG. 13a. $Pb^{2+}$ induced a very strong fluorescence enhancement while $Cu^{2+}$ and $Hg^{2+}$ generated blue-shifts of ca. 100 nm. $Ag^+$ caused a red-shift of ~50 nm, and $Cr^{3+}$ broadened the spectrum by the appearance of a new peak at ~440 nm. Such a diversity of responses establishes that different metals can have markedly different electronic interactions with the ground and/or excited states of a single ODF sensor. Since the oligomer contains only one obvious ligand (L2), this suggests that different electronic properties induced in the metal-ligand complex interact differently with the neighboring chromophores to produce distinct outcomes.

Comparisons of Sensor Sequences. Comparisons of the fluorescence spectra (FIG. 13) of one oligomer to another revealed that their responses were quite distinct from each other. For example, with oligomers 1 and 2, $Co^{2+}$, $Ni^{2+}$, $Ag^+$, $Pb^{2+}$, and $Cu^{2+}$ induced very different responses from the two oligomers. $Co^{2+}$ and $Ni^{2+}$ induced little to no responses from 1. In 2, $Co^{2+}$ and $Ni^{2+}$ induced fluorescence quenching, and $Pb^{2+}$ broadened the spectrum to the shorter wavelengths instead of a very strong enhancement as in 1. $Cu^{2+}$ and $Ag^+$ caused strong quenching in 2; however, in 1, $Cu^{2+}$ resulted in a strong blue-shift ca. 100 nm, and $Ag^+$ induced a red-shift ca. 50 nm. The only metal that did not induce a response in any of the oligomers is $Fe^{3+}$, which may be due to the lack of oxygen-bearing ligands capable of binding the more oxophilic metal. Although $Fe^{3+}$ did not induce a response in any of the oligomers, $Fe^{3+}$ can still be distinguished from the other metal ions in this analyte set by using sensors in which $Fe^{3+}$ is the only metal that did not respond (such as 2, 3 and 4; FIG. 13).

Closer examination of sequences and responses of the sensors is revealing, particularly in several cases where the components varied by only one monomer. For example, sequences 1 and 3 vary by one monomer (ligand L1 in 3 vs an extra H monomer in 1). Comparisons of responses (rows 1 and 3 in FIG. 14) shows that the main differences are strong light-up responses to $Hg^{2+}$, $Pb^{2+}$ and $Ag^+$ in 1 that are absent in 3. This suggests that the extra terphenyl (H) monomer in 1 is central to the mechanism of emission enhancement. Intriguingly, the wavelengths of enhancement lie far to the red of the emission of the terphenyl monomer alone (which emits at 345 nm). A second comparison can be made between sensors 3 and 6; 3 contains an H monomer while 6 contains a nonfluorescent S spacer monomer instead. Although the overall response patterns of the two are similar (rows 3 and 6 in FIG. 14), large light-up responses with $Cu^{2+}$ and $Cr^{3+}$ are seen for 3, which is absent in 6. This establishes the H monomer in 3 as being important in this light-up response as well. Presumably the terphenyl induces this type of response indirectly, perhaps by its interaction with the neighboring ligand fluorophores, which emit at longer wavelengths.

Another interesting comparison can be made between sensors 3, 4 and 5. A strong fluorescence enhancement response with $Ag^+$ is seen for oligomers 4 and 5, which are the only sensors in the set that contain an L3 monomer (FIG. 13). Oligomer 3, which only varies by one monomer from 4 (D monomer in 3 vs ligand L3 monomer in 4), does not display this enhancement. This suggests that ligand L3 is important in the binding and/or light-up response for $Ag^+$.

Although the site of metal ion binding is not yet known for these sensors, the sequences yield some clues in this regard. The combinatorial library was not biased to include at least one ligand monomer for each sequence; however, the selected sequences (1-6) all contained at least one ligand monomer. This suggests that the ligands are important or required for the ODFs to bind the metal ions. Oligomers 1 and 2 have only one clear ligand each (L1 and L2, respectively), which suggests these as a likely site of binding. Oligomers 3, 5, and 6 each have two ligands, while sensor 4 has all three different ligands; thus one or more ligands may be involved in metal recognition. We also note that the binding stoichiometry may involve one sensor per metal or perhaps higher ratios; future work will address the sites and modes of binding in detail. To obtain a preliminary measure of the binding ability (and sensitivity) of sensors 1-6, selected oligomers and metal ions were titrated. The apparent dissociation constants ($K_d$) ranged from 0.64 to 7.66 µM, and the responsive ranges generally cover concentrations varying from ca. 100 nM and above.

Pattern Responses. Because the response profiles of the oligomers are distinct from each other, it is possible to differentiate the set of quenching metal ions using a combination of the responses from a small set of sensors (see below for details). 1, 2, 3 and 4 are particularly useful in this regard because the majority of the metal ions in the set induce a response in these oligomers, the responses are different for the different metal ions, and the response profiles of the sensors are different from each other. In contrast, 6 is not as useful for differentiation because its response diversity is limited (primarily to degrees of quenching), making it difficult to distinguish the metals from one another.

The fluorescence response profiles of the oligomers (FIG. 13) suggest that two (1 and 2) or three (1-3) sensors can be used as a set to differentiate all eight quenching metal ions. Oligomer 1 can be used to distinguish $Pb^{2+}$, $Cu^{2+}$, $Cr^{3+}$, $Ag^+$, and $Hg^{2+}$ from each other and the other metal ions. Notably, oligomer 1 is the only sensor with a blue-shift response to $Hg^{2+}$; in the remaining sensors (2-5), $Hg^{2+}$ induces fluorescence quenching. This allows the differentiation of $Hg^{2+}$ from $Co^{2+}$ and $Ni^{2+}$, which is otherwise difficult because of the common quenching response. The most difficult metal ions to differentiate with the oligomer set (Table 3) were $Co^{2+}$ and $Ni^{2+}$; however, 2 can be used to distinguish the two metals based on stronger the degree of quenching by $Ni^{2+}$. In addition, oligomer 3 can be used to distinguish $Fe^{3+}$ from the other metals, as well as increase the differentiation confidence of the other metal ions.

Figure 15:
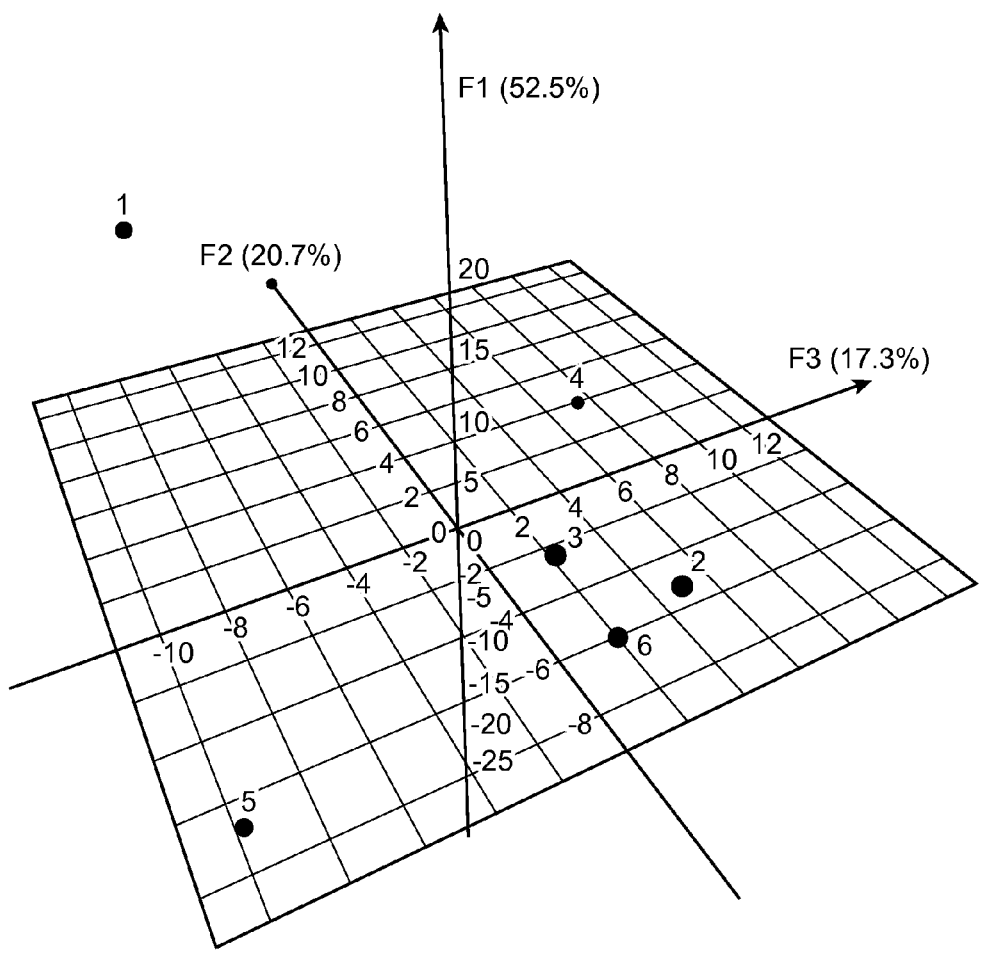
FIG. 15. PCA plot of oligomers 1-6 based on their responses (difference spectra profile data) to all the metal ions.

Chemometric Analysis. Principal component analysis (PCA) and agglomerative hierarchical clustering (AHC) were performed on the data to quantitatively evaluate our observations and better understand the relationships in the sensor responses. To carry out these quantitative analyses, we input the delta(intensity) values from the 48 difference spectra taken at 10 nm increments into the analytical software (XLSTAT). Chemometric analysis was first performed on oligomers 1-6 based on their responses to all the metal ions in order to examine how different the sensors' overall responses are from each other. PCA plots are shown in FIG. 15, illustrating the scatter in the responses of the oligomers to the metal ions. The responses from oligomers 1, 4 and 5 to the metal ions show very good scattering, indicating that the response of each of these oligomers to the set of quenching metal ions is very different from the other sensors. Oligomers 2, 3 and 6 were clustered more closely together (with 2 and 6 the closest). Although the overall response profiles of oligomers 2, 3 and 6 showed some similarity (FIGS. 13b, c and f respectively), several prominent differences can be observed: the main differences in sensor 3 from 2 and 6 are the peak at ca. 440 nm (from $Cu^{2+}$ and/or $Cr^{3+}$) and the red-shift induced by $Ag^+$; and the major difference between oligomer 2 and 6 is the light-up peak (ca. 440 nm) from $Cr^{3+}$ that is absent in 6. PCA did not capture these differences in the first three principal component axes (F1, F2 and F3); however, the differences were clear in the fourth principal component, F4.

Figure 16:
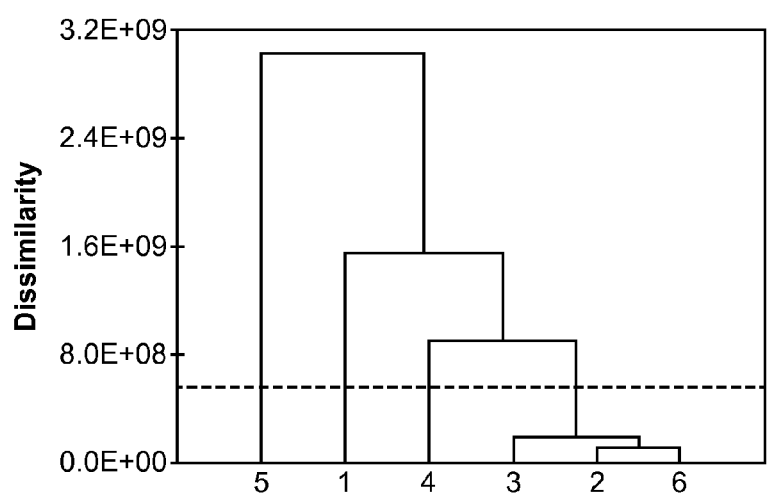
FIG. 16. AHC dendrogram of oligomers 1-6 based on their responses (difference spectra profile data) to all the metal ions.

AHC analysis was also performed on oligomers 1-6 based on their responses to all the metal ions. The AHC analysis allowed us to generate a dendrogram of families of sensors according to their response profile to the eight quenching metal ions (FIG. 16). Four most dissimilar classes of sensor responses were found; 1, 4 and 5 were categorized into their own class, while 2, 3 and 6 were grouped together into one class. From the set of six sensors, the response profile of oligomer 5 is the most different from the other sensors, followed by 1 and then 4. The sensors that exhibited a more similar response profile were again oligomers 2, 3 and 6, with 3 being more different from 2 and 6, which corroborates the results above.

Figure 17:
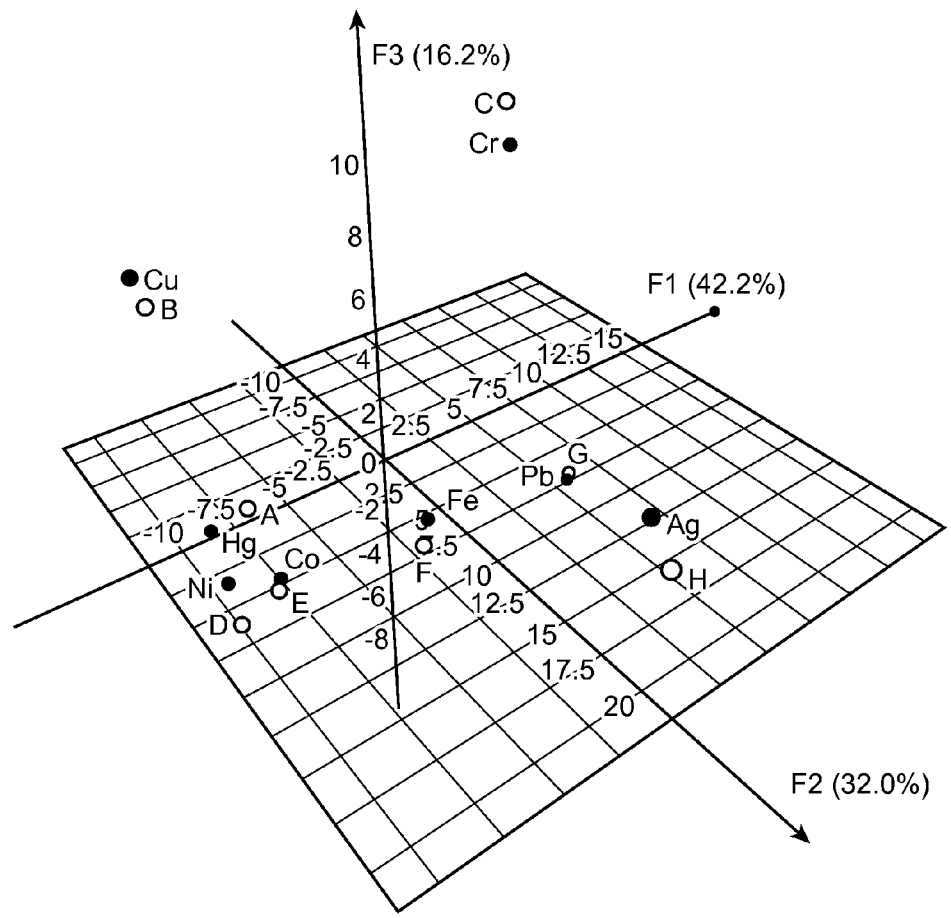
FIG. 17. PCA plot of the quenching metal ions based on the difference spectra profile data of sensors 1-5. Data for the known and unknown metal ion solutions (discussed below) were included in the analysis to facilitate direct comparison. Blue color=known metal solutions and red color=unknown metal solutions A-H.

A second chemometric analysis was performed on the quenching metal ions based on the difference spectra profile data of oligomers 1-5 in order to investigate the ability of sensors to differentiate the metal ions based on response patterns. Because the response diversity of oligomer 6 is limited primarily to degrees of quenching (which makes 6 not as useful as sensors 1-5), sensor 6 was dropped from further analyses. The PCA results are shown in FIG. 17, illustrating the scatter in the responses induced by the metal ions. Overall, the findings correspond well with the qualitative observations. The responses from oligomers 1-5 induced by $Cu^{2+}$, $Pb^{2+}$, $Ag^+$, $Cr^{3+}$, and $Fe^{3+}$ showed very good scattering. Therefore, allowing these five metal ions to be easily distinguished from the remaining three metal ions, $Hg^{2+}$, $Co^{2+}$, and $Ni^{2+}$, which were clustered more closely together. However, oligomer 1 was able to discriminate $Hg^{2+}$ (by a blue-shift) from $Co^{2+}$ and $Ni^{2+}$ (which caused little to no response). In the remaining sensors 2-5, $Hg^{2+}$, $Co^{2+}$, and $Ni^{2+}$ all quenched the fluorescence. Fortunately, the degrees of quenching in 2 and 4 were different for these metal ions, which could be used to distinguish $Co^{2+}$ from $Ni^{2+}$.

Figure 18:
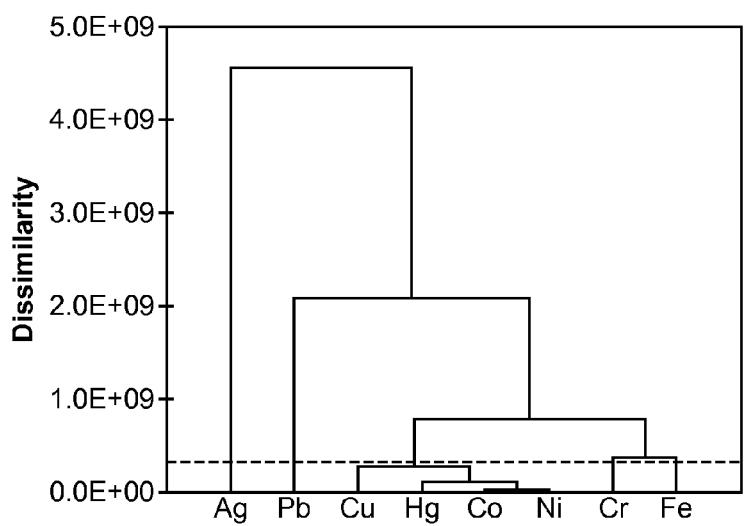
FIG. 18. AHC dendrogram of the quenching metal ions based on the difference spectra profiles of sensors 1-5.

AHC analysis was also performed on the metal ions based on the difference spectra data of sensors 1-5. This allowed us to generate a dendrogram of families of metal ions according to the response pattern they induce in oligomers 1-5 (FIG. 18). The AHC results also corroborated the qualitative observations, discussed above. From the set of eight metal ions, $Ag^+$ induced the most different pattern of responses from the sensors, followed by $Pb^{2+}$ and then $Cr^{3+}$ and $Fe^{3+}$. The metals ($Cu^{2+}$, $Hg^{2+}$, $Co^{2+}$, and $Ni^{2+}$) that show the general tendency to quench oligomers 1-5 were grouped together into one class. In this class, $Cu^{2+}$ is the most different from the other metal ions in its responses, followed by $Hg^{2+}$. The most similar (i.e., difficult to differentiate) metals were again $Co^{2+}$ and $Ni^{2+}$, as previously observed (see first and second vertical rows in FIG. 14).

Identification of Unknowns. As a proof of principle, we performed a blind study to test whether a set of these sensors could be used to distinguish these metals without prior knowledge of their identity. Thus we measured the sensor responses with eight unknown samples containing the fluorescent quenching metal ion set ($Co^{2+}$, $Ni^{2+}$, $Hg^{2+}$, $Pb^{2+}$, $Ag^+$, $Cr^{3+}$, and $Fe^{3+}$). Although only two (1 and 2) or three sensors (1-3) can be used to distinguish the eight metal ions, oligomers 4 and 5 were included to enhance the identification confidence. The difference spectra profiles for each sensor with the unknown solutions were then plotted. The difference spectra profiles gave nearly identical, overlapping spectral responses with the previously measured known metal solutions. Thus all eight unknown metal ions were correctly identified by simply comparing the difference spectra profiles of the unknown solutions to the known solutions.

Chemometric tools were also used to simplify the identification of the unknown metal ion solutions. In the PCA scatter plot (FIG. 17), the difference spectra profiles of the unknown solutions were also included. PCA was useful in condensing the dimensionality of the data set, thus facilitating the identification of the unknown solutions. The results show a very good clustering of the unknowns with the known samples, where each unknown paired closely with the correct known sample identity. Moreover, the close pairing also indicates good reproducibility of the results and methods.

In addition to the AHC analysis on the known metal solution data alone (FIG. 18), AHC analysis including both known and unknown solution data was also performed. Similar to the PCA, the AHC results show pairing of each unknown samples with a known metal sample; and again this pairing correspond to the correct identity of the unknown metal ion solutions. The low level of dissimilarity of each of the unknown-known pair indicates that each pair is highly similar.

Figure 19:
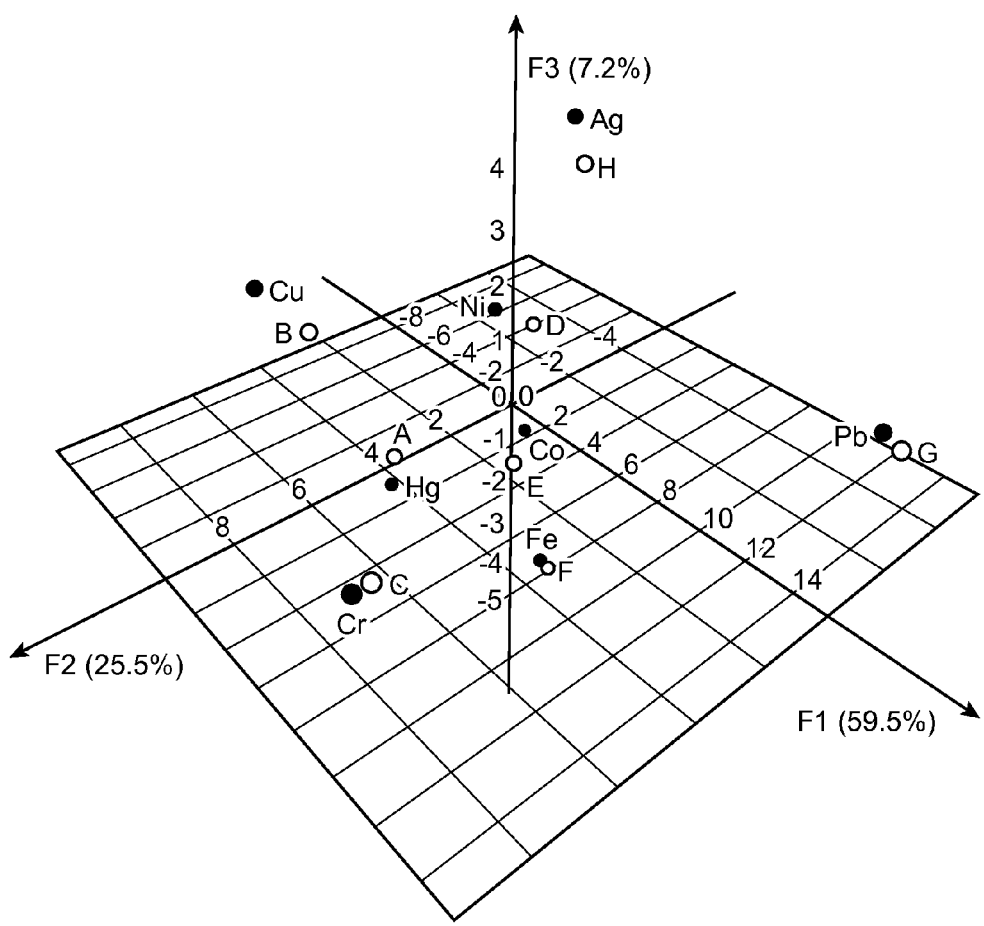
FIG. 19. PCA plot of the quenching metal ions based on sensors 1 and 2. Data for the known and unknown metal ion solutions were included in the analysis to facilitate direct comparison. Blue color=known metal solutions and red color=unknown metal solutions A-H.

In order to test the possibility of using as few as two sensors to differentiate the metal ion set, PCA analysis was performed with oligomers 1 and 2. The PCA result from using only these two sensors (FIG. 19) reveals very good scattering among the metal ions, and close pairing of each unknown sample response with that of a known metal sample. The analysis results in correct assignment of all the unknowns, indicating that the eight metal ions can be differentiated by the combined responses of the two sensors 1 and 2.

Design Features. An examination of the present sensor design points out some notable differences from other recently reported metal sensor arrays. Previous work by Anzenbacher employed a water insoluble 8-hydroxyquinoline receptor attached to various conjugated chromophores in the differentiation of transition metals by quenching or enhancement responses. Anslyn has reported the use of a squaraine dye with varied thiols in degassed DMSO to differentiate five heavy metals by increases and decreases in fluorescence intensity. Dordick has described the use of fifteen polyphenol polymers to distinguish four metals by varied quenching and enhancement responses. Wolfbeis employed commercial dyes and a fluorescence lifetime-based approach to distinguishing five metals.

Compared to previous approaches, the current ODF sensor design offers benefits of water solubility, a higher diversity of responses, and versatility of use. The charged DNA phosphodiester backbone enables even hydrophobic components (fluorophores, ligands, linkers, etc.) to be utilized as building blocks for the sensors; and the water solubility of the sensors avoids problems associated with the incompatibility of hydrophobic sensors and hydrophilic cations. Second, we have observed a considerably greater variation in responses, with not only strong enhancements and quenching, but also wavelength shifts of as much as 110 nm. This diversity of response allows the use of fewer sensors in distinguishing a greater number of metals. In contrast, some previous responses yielded only simple quenching for the commonly quenching metals, and relied instead on varied degrees of quenching or varied lifetimes. Finally, the current approach offers considerably versatility. For example, all the ODFs are excited at a single wavelength, thus requiring only one spectral measurement with a single filter set. In addition, although the sensing results here were obtained in solution (which makes more thorough characterization possible), the ODF design could also be adapted readily for application on solid supports, as the original screening (which showed similar spectral changes) was carried out on PEG-polystyrene beads (FIG. 12). ODFs on PEG-polystyrene beads have already been shown to be functional sensors for small molecule vapors.

Another noteworthy aspect of the present experimental design strategy is the combinatorial library method for sensor discovery, which considerably enhances efficiency. Utilizing the DNA backbone allows the use of an automated synthesizer, resulting in rapid library assembly as well as rapid re-synthesis. The iterative synthesis makes it possible to generate a large set of potential sensors from a small set of precursor monomers (4,096 different tetramers in the present case). By simultaneously screening through a large sensor set, discovery of strong and varied responders is rapid, and weak responders are quickly eliminated as candidates. The varied combinations of binding and transducing elements in the library are arranged in many possible sequences, thus allowing for a large diversity of possible mechanisms of metal binding and signal transduction.

In summary, we have demonstrated a new molecular design for differentiating a set of fluorescence-quenching metal ions ($Co^{2+}$, $Ni^{2+}$, $Cu^{2+}$, $Hg^{2+}$, $Pb^{2+}$, $Ag^+$, $Cr^{3+}$, and $Fe^{3+}$) based on the response diversity of a small set of sensors composed of polyfluorophores on a DNA backbone. The design allows the ligands and fluorophores to interact with each other on a DNA backbone, enabling the overall properties of the oligomers to be different from those of the monomers. The advantages that the ODF-based design offers include highly diverse responses, water solubility, and a single excitation wavelength for the whole set of sensors. In addition, the modular nature of the design enables rapid synthesis and discovery of sensors from libraries.

Using the present molecular design strategy, sensors were identified that have a wide variety of responses to quenching metal ions beyond simple quenching of fluorescence. Because of the diversity of sensor responses, as few as two sensors (1 and 2) can be used to differentiate all eight metal ions in the set. The modular nature of this sensor design strategy provides a broadly applicable approach to finding sensors for differentiating many different cations by pattern-based recognition, simply by varying the sequence and composition of ligands and fluorophores using a DNA synthesizer.

What is claimed is:
1. A sensor for a target analyte having the structure:

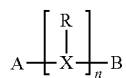

wherein A and B are each independently a backbone group, linker, or a substrate, and may be absent or present;

each X is a backbone group independently selected from a sugar-phosphate, a phosphodiester, a phosphorothioate, a phosphotriester, a locked nucleic acid (LNA) backbone group, a morpholino, a 2'-O-methyl RNA or a peptide nucleic acid backbone group;

n is 2 to 20; and each R is independently a spacer, or one of the following structures:

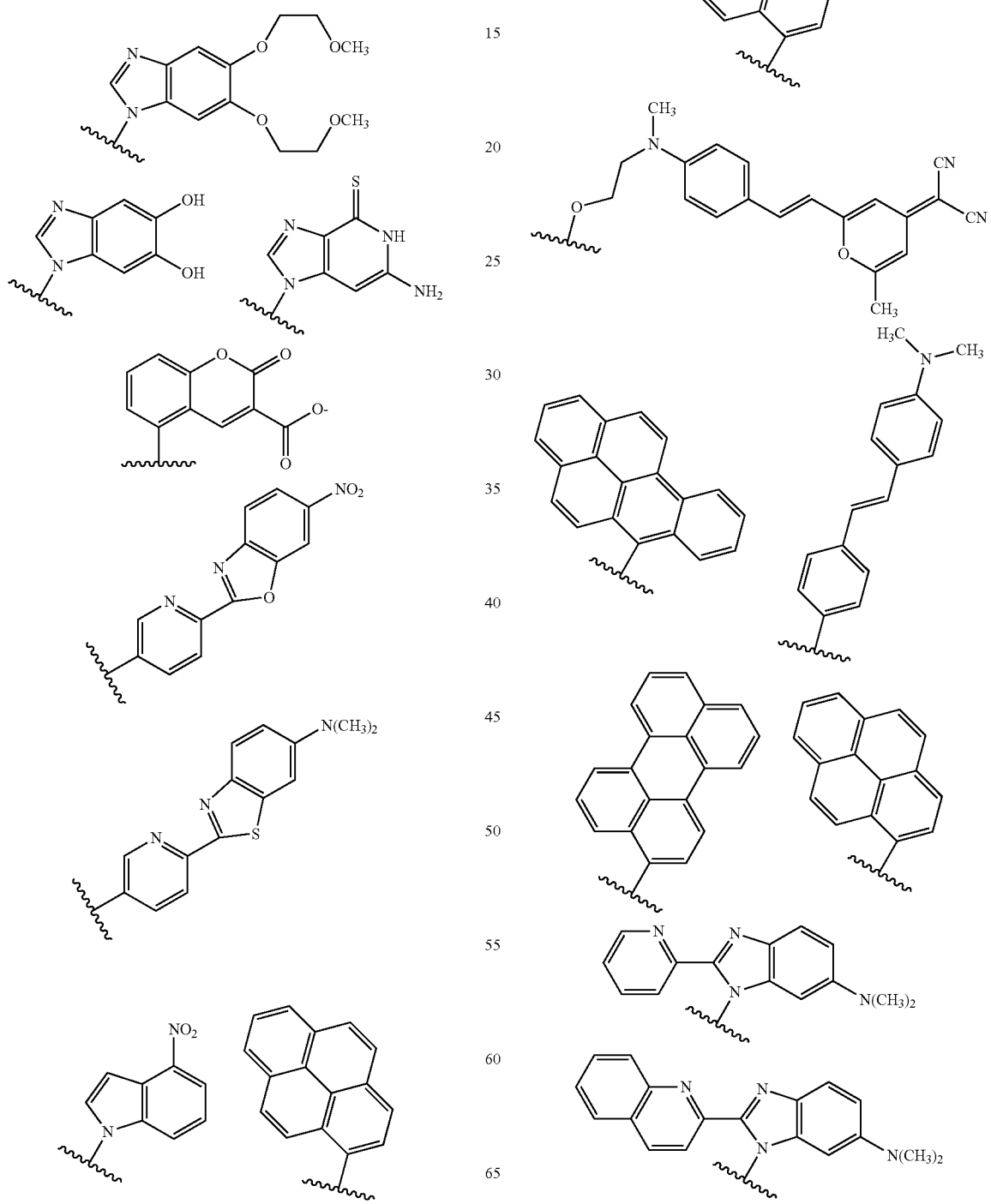

-continued

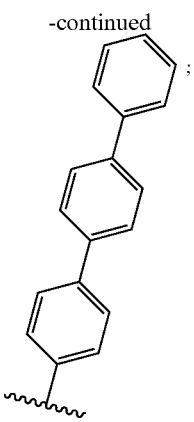

wherein at least one R is a ligand for a metal ion, a quencher or a spacer, wherein the sensor lacks a natural DNA or RNA base; and
wherein the sensor binds a target analyte that is selected from a metal ion and a neutral organic molecule.

2. The sensor of claim 1, wherein at least one R is a ligand for a metal ion.

3. The sensor of claim 1, wherein X is ribosephosphate or deoxyribosephosphate such that the backbone groups Xn comprise a DNA or RNA backbone, and wherein R is connected to X via the C1 position of the ribose or deoxyribose.

4. The sensor of claim 1 further comprising:
at least one bound metal ion.

5. The sensor of claim 1, whereby the fluorescence emission wavelength of the sensor changes following binding of a the target analyte.

6. The sensor of claim 1, wherein said target analyte is a neutral organic molecule in the vapor phase.

7. The sensor of claim 2 wherein:
said target analyte is a metal ion.

8. The sensor of claim 7 wherein:
said metal ion is $Zr^{4+}$, $Hf^{4+}$, $V^{3+}$, $Cr^{3+}$, $Mo^{3+}$, $W^{4+}$, $Mn^{2+}$, $Ru^{3+}$, $Os^{3+}$, $Co^{3+}$, $Ni^{2+}$, $Pd^{2+}$, $Pt^{2+}$, $Cu^{2+}$, $Ag^+$, $Zn^{2+}$, $Cd^{2+}$, $Hg^{2+}$, $Be^{2+}$, $Ba^{2+}$, $Al^{3+}$, $In^{3+}$, $Tl^+$, $Ge^{4+}$, $Sn^{4+}$, $Pb^{2+}$, $As^{3+}$, $Sb^{5+}$, $Se^{4+}$, $Fe^{2+}$, $Fe^{3+}$, $Au^+$, $Au^{3+}$, $Te^{2+}$ or $UO_2^{2+}$, $Li^+$, $Na^+$, $K^+$, $Rb^+$, $Cs^+$, $Mg^{2+}$, $Ca^{2+}$, $Sr^{2+}$, $La^{3+}$, $Ce^{3+}$, $Pr^{3+}$, $Nd^{3+}$, $Sm^{3+}$, $Eu^{3+}$ $Gd^{3+}$, $Tb^{3+}$, $Ho^{3+}$, $Dy^{3+}$, $Er^{3+}$, $Tm^{3+}$, $Yb^{3+}$, $Lu^{3+}$.

9. The sensor of claim 6 wherein:
said neutral organic molecule is a petroleum component, a petroleum additive, a sulfur compound found in oil, a cleaner/degreaser, a solvent, a polychlorinated hydrocarbon, a pesticide or a herbicide.

10. The sensor of claim 1, wherein: said sensor is linked to a substrate through A or B.

11. A method for detection of an analyte of interest, the method comprising:
contacting a sample suspected of comprising said analyte of interest with the sensor according to claim 1, for a time and under conditions sufficient to permit binding of said analyte of interest to said sensor; and detecting a change in fluorescence emission intensity or emission wavelength of said sensor.

12. The sensor of claim 1, wherein n is from 2 to 8.

13. The sensor of claim 12, wherein at least one R is selected from one of the following structures:

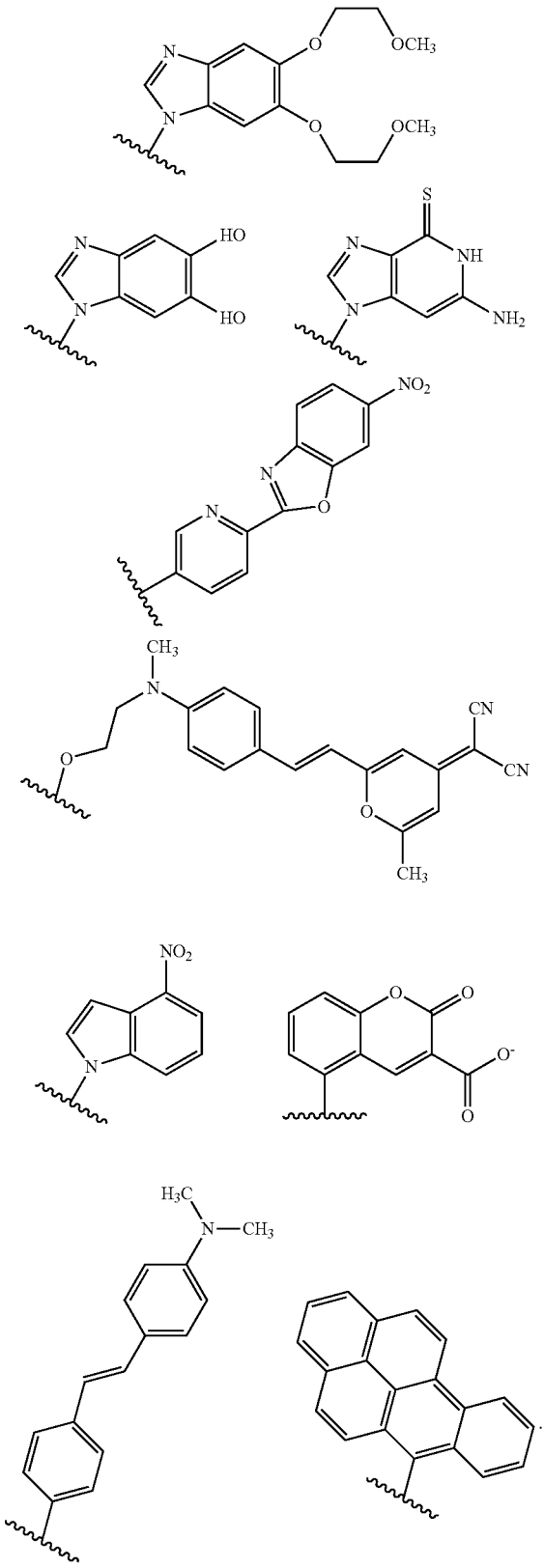

14. The sensor of claim 13, wherein X is ribosephosphate or deoxyribosephosphate such that the backbone groups Xn comprise a DNA or RNA backbone, and wherein R is connected to X via the C1 position of the ribose or deoxyribose.

15. The sensor of claim 14, wherein n is 4.

16. The sensor of claim 15, wherein the target analyte is a neutral organic molecule in the vapor phase.

* * * * *